(12) United States Patent
Rofougaran

(10) Patent No.: US 8,254,853 B2
(45) Date of Patent: Aug. 28, 2012

(54) BIO-MEDICAL UNIT HAVING STORAGE LOCATION INFORMATION

(75) Inventor: Ahmadreza (Reza) Rofougaran, Newport Coast, CA (US)

(73) Assignee: Broadcom Corporation, Irvine, CA (US)

( * ) Notice: Subject to any disclaimer, the term of this patent is extended or adjusted under 35 U.S.C. 154(b) by 110 days.

(21) Appl. No.: 12/848,823

(22) Filed: Aug. 2, 2010

(65) Prior Publication Data

US 2011/0076983 A1 Mar. 31, 2011

Related U.S. Application Data

(60) Provisional application No. 61/247,060, filed on Sep. 30, 2009.

(51) Int. Cl.
*H04B 1/034* (2006.01)
(52) U.S. Cl. ............... 455/100; 455/404.1; 455/573; 705/3
(58) Field of Classification Search .......... 455/100, 455/404.1, 573, 41.2, 414.1, 404.2; 705/3, 705/2; 714/15
See application file for complete search history.

(56) References Cited

U.S. PATENT DOCUMENTS

| | | | |
|---|---|---|---|
| 6,572,564 B2 * | 6/2003 | Ito et al. .................... | 600/573 |
| 6,643,542 B1 * | 11/2003 | Kawanishi .................. | 600/547 |
| 6,957,167 B2 * | 10/2005 | Kawanishi et al. ......... | 702/173 |
| 7,125,382 B2 | 10/2006 | Zhou et al. | |
| 7,193,712 B2 * | 3/2007 | Sottery et al. .............. | 356/369 |
| 7,241,266 B2 | 7/2007 | Zhou et al. | |
| 7,266,269 B2 | 9/2007 | Koste et al. | |
| 7,418,121 B2 * | 8/2008 | Kasai .......................... | 382/128 |
| 7,720,701 B2 * | 5/2010 | Richards et al. ............ | 705/4 |
| 7,863,188 B2 * | 1/2011 | Tsurume et al. ............ | 438/667 |
| 8,007,436 B2 * | 8/2011 | Katayama .................. | 600/301 |
| 2001/0031913 A1 * | 10/2001 | Ito et al. ..................... | 600/300 |
| 2003/0037054 A1 * | 2/2003 | Dutta et al. ................. | 707/100 |
| 2004/0015056 A1 * | 1/2004 | Shinoda ...................... | 600/300 |
| 2004/0057340 A1 * | 3/2004 | Charles-Erickson et al. | 368/10 |
| 2004/0113771 A1 * | 6/2004 | Ozaki et al. ............. | 340/539.12 |
| 2004/0212515 A1 * | 10/2004 | Eaton et al. ............. | 340/870.07 |
| 2005/0093973 A1 * | 5/2005 | Hibi et al. ................... | 348/71 |
| 2005/0100977 A1 * | 5/2005 | Yang et al. .................. | 435/11 |
| 2006/0082773 A1 * | 4/2006 | Sottery et al. ............... | 356/369 |
| 2006/0217921 A1 * | 9/2006 | Kourogi et al. ............. | 702/150 |

(Continued)

OTHER PUBLICATIONS

Arjang Hassibi, et al., "A Spectral-Scanning Nuclear Magnetic Resonance Imaging (MRI) Transceiver", IEEE Journal of Solid-State Circuits, Jun. 2009, pp. 1805-1813, vol. 44, No. 6.

(Continued)

*Primary Examiner* — Minh D Dao
(74) *Attorney, Agent, or Firm* — Garlick & Markison; Bruce E. Garlick

(57) ABSTRACT

A bio-medical unit includes a power harvesting module, a processing module, memory, and a transceiver. The power harvesting module converts an electromagnetic signal into a supply voltage, which powers the processing module, the memory, and the transceiver. The processing module communicates, via the transceiver, with an external device regarding a medical matter to obtain storage location information regarding the medical matter, wherein the storage location information indicates where data associated with the medical matter is at least partially stored. The processing module then aggregates the storage location information with patient data storage location information to produce updated patient data storage location information, wherein the patient data storage location information contains storage location information regarding previous medical matters associated with the host body. The memory stores the patient data storage location information and the updated patient data storage location information.

20 Claims, 19 Drawing Sheets

U.S. PATENT DOCUMENTS

| | | | | |
|---|---|---|---|---|
| 2007/0023758 | A1* | 2/2007 | Tsurume et al. | 257/66 |
| 2007/0050213 | A1* | 3/2007 | Matsushima et al. | 705/3 |
| 2009/0077024 | A1* | 3/2009 | Abraham-Fuchs et al. | 707/3 |
| 2009/0105552 | A1* | 4/2009 | Nishiyama et al. | 600/300 |
| 2010/0053315 | A1* | 3/2010 | Miura et al. | 348/77 |
| 2010/0256992 | A1* | 10/2010 | Roberts et al. | 705/3 |
| 2012/0010867 | A1* | 1/2012 | Eder | 703/13 |

OTHER PUBLICATIONS

John E. Speich, et al., "Medical Robotics", Encyclopedia of Biomaterials and Biomedical Engineering, 2004, pp. 983-992, Marcel Dekker, Inc.

Eric Freudenthal, et al., "Evaluation of HF RFID for Implanted Medical Applications", Apr. 16, 2006, 4 pp.

Gibson, Ultrasound as a Proposed Drug Release Mechanism in Biomedical Microrobots, Arizona Space Grant Consortium, Univ. of Arizona Advanced Microsystems Laboratory, Dept. of Aerospace and Mechanical Engineering, Apr. 19, 2008, 17 pages.

Marin Soljacic et al., "WiTricity: Non-Radiactive Wireless Power Transfer," Oct. 9, 2008, 56 pages.

Robert E. Carlson, Ph.D., et al., "Development of an Implantable Glucose Sensor," Dec. 4, 2007, 16 pages.

Shekhar Bhansali, "Role of MEMS and Nanotechnology in Medical Technologies," University of South Florida, Mar. 1, 2004, 29 pages.

* cited by examiner

BIO-MEDICAL UNIT HAVING STORAGE LOCATION INFORMATION

CROSS REFERENCE TO RELATED PATENTS

This patent application is claiming priority under 35 USC §119 to a provisionally filed patent application entitled BIO-MEDICAL UNIT AND APPLICATIONS THEREOF, having a provisional filing date of Sep. 30, 2009, and a provisional Ser. No. 61/247,060.

STATEMENT REGARDING FEDERALLY SPONSORED RESEARCH OR DEVELOPMENT

NOT APPLICABLE

INCORPORATION-BY-REFERENCE OF MATERIAL SUBMITTED ON A COMPACT DISC

NOT APPLICABLE

BACKGROUND OF THE INVENTION

1. Technical Field of the Invention

This invention relates generally to medical equipment and more particularly to wireless medical equipment.

2. Description of Related Art

As is known, there is a wide variety of medical equipment that aids in the diagnosis, monitoring, and/or treatment of patients' medical conditions. For instances, there are diagnostic medical devices, therapeutic medical devices, life support medical devices, medical monitoring devices, medical laboratory equipment, etc. As specific exampled magnetic resonance imaging (MRI) devices produce images that illustrate the internal structure and function of a body.

The advancement of medical equipment is in step with the advancements of other technologies (e.g., radio frequency identification (RFID), robotics, etc.). Recently, RFID technology has been used for in vitro use to store patient information for easy access. While such in vitro applications have begun, the technical advancement in this area is in its infancy.

BRIEF SUMMARY OF THE INVENTION

The present invention is directed to apparatus and methods of operation that are further described in the following Brief Description of the Drawings, the Detailed Description of the Invention, and the claims. Other features and advantages of the present invention will become apparent from the following detailed description of the invention made with reference to the accompanying drawings.

BRIEF DESCRIPTION OF THE SEVERAL VIEWS OF THE DRAWING(S)

DETAILED DESCRIPTION OF THE INVENTION

Figure 1:
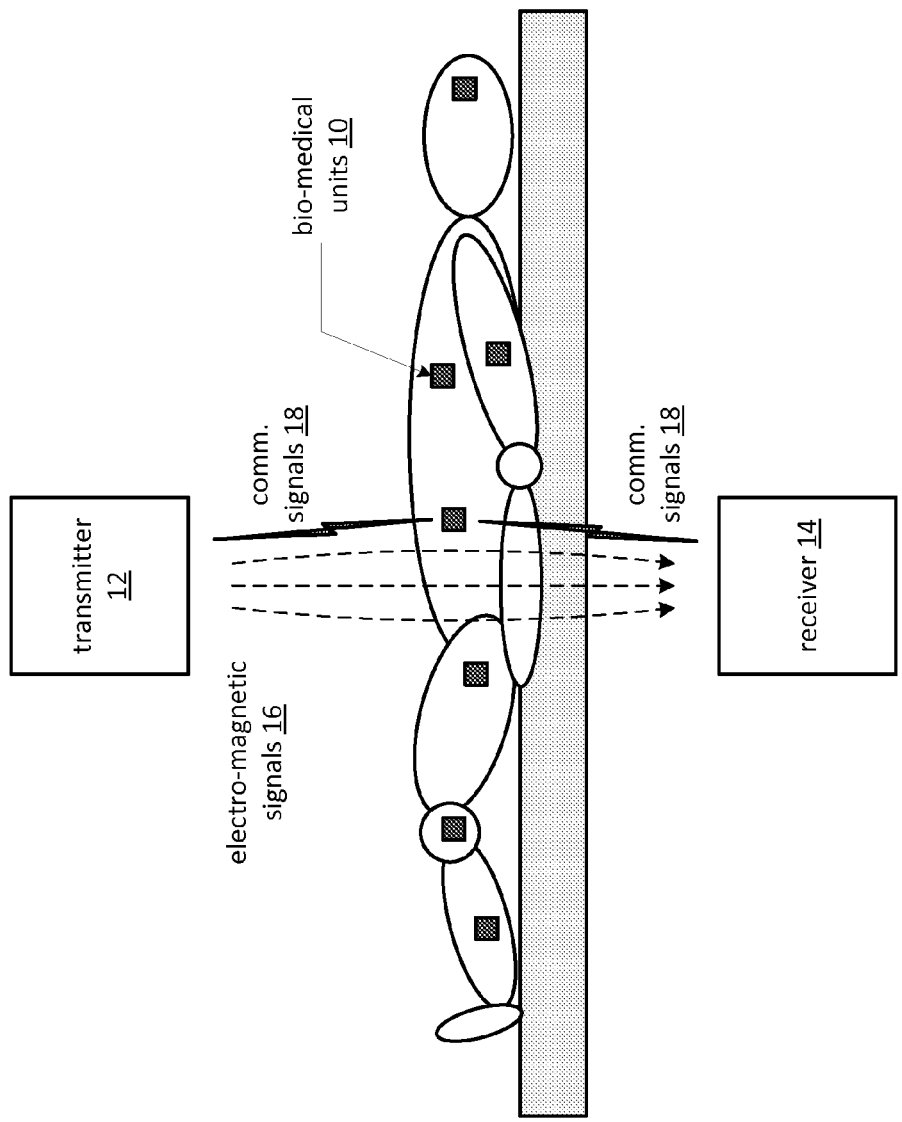
FIG. 1 is a diagram of an embodiment of a system in accordance with the present invention.

FIG. 1 is a diagram of an embodiment of a system that includes a plurality of bio-medical units 10 embedded within a body and/or placed on the surface of the body to facilitate diagnosis, treatment, and/or data collections. Each of the bio-medical units 10 is a passive device (e.g., it does not include a power source (e.g., a battery)) and, as such, includes a power harvesting module. The bio-medical units 10 may also include one or more of memory, a processing module, and functional modules. Alternatively, or in addition to, each of the bio-medical units 10 may include a rechargeable power source.

In operation, a transmitter 12 emits electromagnetic signals 16 that pass through the body and are received by a receiver 14. The transmitter 12 and receiver 14 may be part of a piece of medical diagnostic equipment (e.g., magnetic resonance imaging (MRI), X-ray, etc.) or independent components for stimulating and communicating with the network of bio-medical units in and/or on a body. One or more of the bio-medical units 10 receives the transmitted electromagnetic signals 16 and generates a supply voltage therefrom. Examples of this will be described in greater detail with reference to FIGS. 8-12.

Embedded within the electromagnetic signals 16 (e.g., radio frequency (RF) signals, millimeter wave (MMW) signals, MRI signals, etc.) or via separate signals, the transmitter 12 communicates with one or more of the bio-medical units 10. For example, the electromagnetic signals 16 may have a frequency in the range of a few MHz to 900 MHz and the communication with the bio-medical units 10 is modulated on the electromagnetic signals 16 at a much higher frequency (e.g., 5 GHz to 300 GHz). As another example, the communication with the bio-medical units 10 may occur during gaps (e.g., per protocol of medical equipment or injected for communication) of transmitting the electromagnetic signals 16. As another example, the communication with the bio-medical units 10 occurs in a different frequency band and/or using a different transmission medium (e.g., use RF or MMW signals when the magnetic field of the electromagnetic signals are dominate, use ultrasound signals when the electromagnetic signals 16 are RF and/or MMW signals, etc.).

One or more of the bio-medical units 10 receives the communication signals 18 and processes them accordingly. The communication signals 18 may be instructions to collect data, to transmit collected data, to move the unit's position in the body, to perform a function, to administer a treatment, etc. If the received communication signals 18 require a response, the bio-medical unit 10 prepares an appropriate response and transmits it to the receiver 14 using a similar communication convention used by the transmitter 12.

Figure 2:
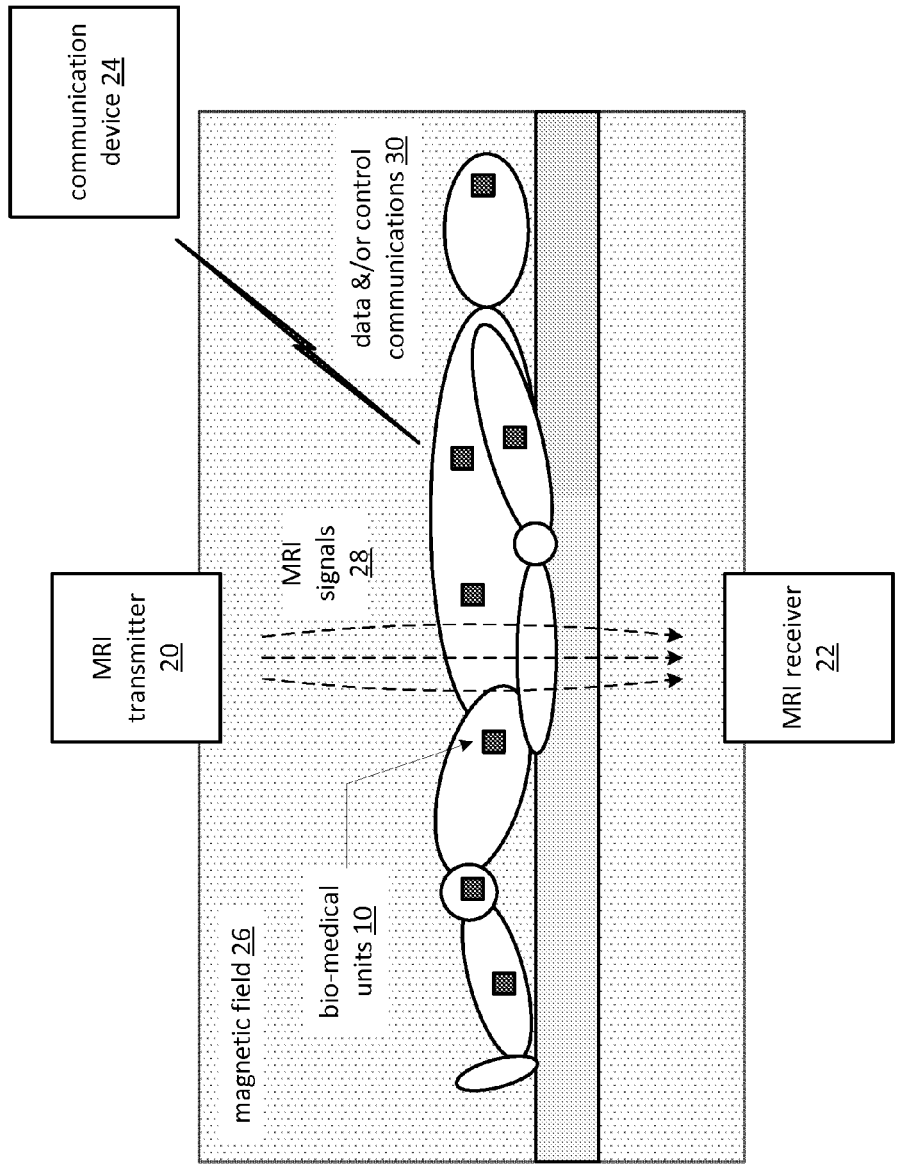
FIG. 2 is a diagram of another embodiment of a system in accordance with the present invention.

FIG. 2 is a diagram of another embodiment of a system that includes a plurality of bio-medical units 10 embedded within a body and/or placed on the surface of the body to facilitate diagnosis, treatment, and/or data collections. Each of the bio-medical units 10 is a passive device and, as such, includes a power harvesting module. The bio-medical units 10 may also include one or more of memory, a processing module, and functional modules. In this embodiment, the person is placed in an MRI machine (fixed or portable) that generates a magnetic field 26 through which the MRI transmitter 20 transmits MRI signals 28 to the MRI receiver 22.

One or more of the bio-medical units 10 powers itself by harvesting energy from the magnetic field 26 or changes thereof as produced by gradient coils, from the magnetic fields of the MRI signals 28, from the electrical fields of the MRI signals 28, and/or from the electromagnetic aspects of the MRI signals 28. A unit 10 converts the harvested energy into a supply voltage that supplies other components of the unit (e.g., a communication module, a processing module, memory, a functional module, etc.).

A communication device 24 communicates data and/or control communications 30 with one or more of the bio-medical units 10 over one or more wireless links. The communication device 24 may be a separate device from the MRI machine or integrated into the MRI machine. For example, the communication device 24, whether integrated or separate, may be a cellular telephone, a computer with a wireless interface (e.g., a WLAN station and/or access point, Bluetooth, a proprietary protocol, etc.), etc. A wireless link may be one or more frequencies in the ISM band, in the 60 GHz frequency band, the ultrasound frequency band, and/or other frequency bands that supports one or more communication protocols (e.g., data modulation schemes, beamforming, RF or MMW modulation, encoding, error correction, etc.).

The composition of the bio-medical units 10 includes non-ferromagnetic materials (e.g., paramagnetic or diamagnetic) and/or metal alloys that are minimally affected by an external magnetic field 26. In this regard, the units harvest power from the MRI signals 28 and communicate using RF and/or MMW electromagnetic signals with negligible chance of encountering the projectile or missile effect of implants that include ferromagnetic materials.

Figure 3:
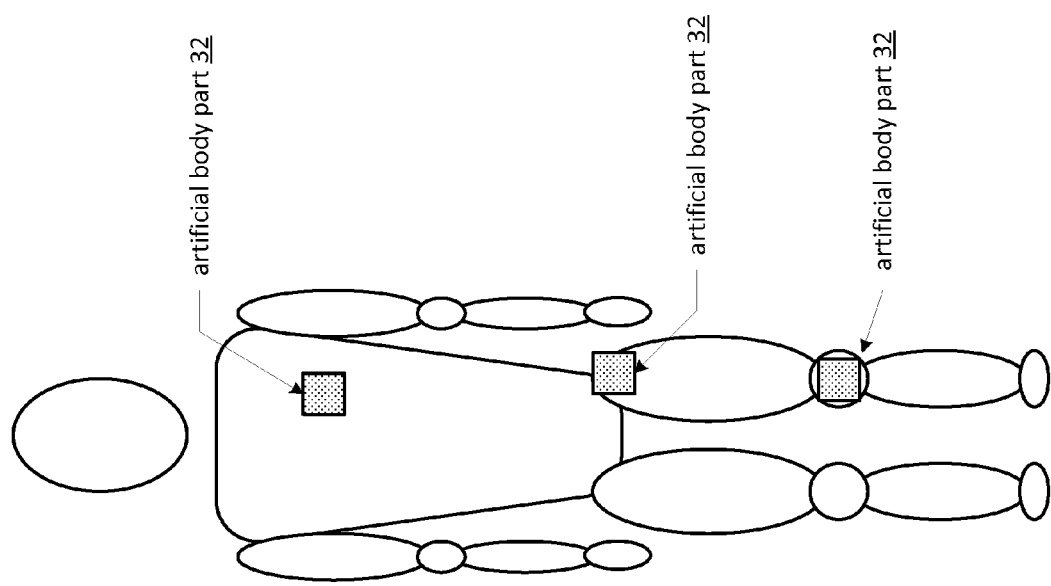
FIG. 3 is a diagram of an embodiment of an artificial body part including one or more bio-medical units in accordance with the present invention.

FIG. 3 is a diagram of an embodiment of an artificial body part 32 including one or more bio-medical units 10 that may be surgically implanted into a body. The artificial body part 32 may be a pace maker, a breast implant, a joint replacement, an artificial bone, splints, fastener devices (e.g., screws, plates, pins, sutures, etc.), artificial organ, etc. The artificial body part 32 may be permanently embedded in the body or temporarily embedded into the body.

Figure 4:
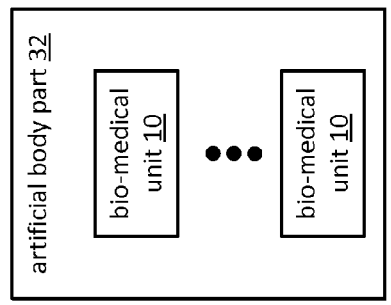
FIG. 4 is a schematic block diagram of an embodiment of an artificial body part in accordance with the present invention.

FIG. 4 is a schematic block diagram of an embodiment of an artificial body part 32 that includes one or more bio-medical units 10. For instance, one bio-medical unit 10 may be used to detect infections, the body's acceptance of the artificial body part 32, measure localized body temperature, monitor performance of the artificial body part 32, and/or data gathering for other diagnostics. Another bio-medical unit 10 may be used for deployment of treatment (e.g., disperse medication, apply electrical stimulus, apply RF radiation, apply laser stimulus, etc.). Yet another bio-medical unit 10 may be used to adjust the position of the artificial body part 32 and/or a setting of the artificial body part 32. For example, a bio-medical unit 10 may be used to mechanically adjust the tension of a splint, screws, etc. As another example, a bio-medical unit 10 may be used to adjust an electrical setting of the artificial body part 32.

Figure 5:
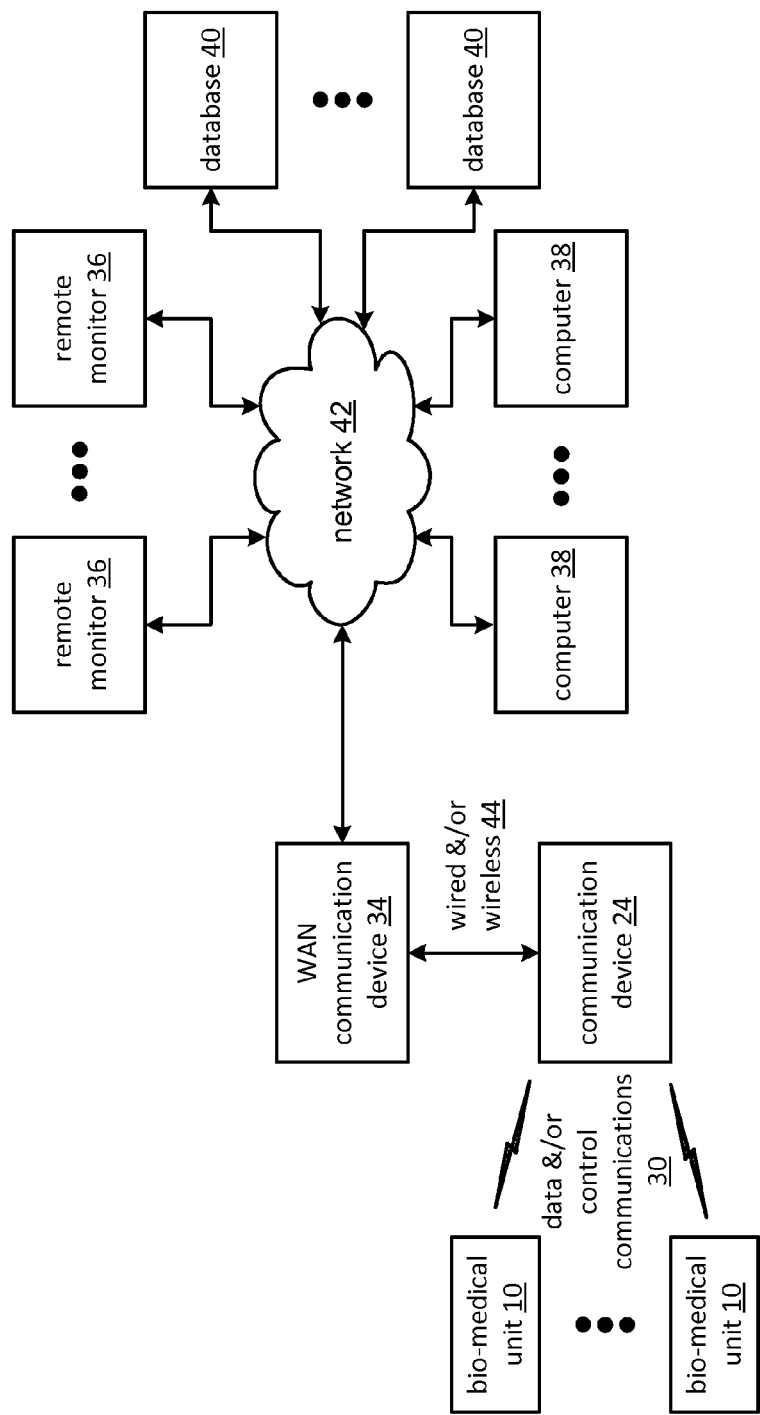
FIG. 5 is a diagram of another embodiment of a system in accordance with the present invention.

FIG. 5 is a diagram of another embodiment of a system that includes a plurality of bio-medical units 10 and one or more communication devices 24 coupled to a wide area network (WAN) communication device 34 (e.g., a cable modem, DSL modem, base station, access point, hot spot, etc.). The WAN communication device 34 is coupled to a network 42 (e.g., cellular telephone network, internet, etc.), which has coupled to it a plurality of remote monitors 36, a plurality of databases 40, and a plurality of computers 38. The communication device 24 includes a processing module and a wireless transceiver module (e.g., one or more transceivers) and may function similarly to communication module 48 as described in FIG. 8, In this system, one or more bio-medical units 10 are implanted in, or affixed to, a host body (e.g., a person, an animal, genetically grown tissue, etc.). As previously discussed and will be discussed in greater detail with reference to one or more of the following figures, a bio-medical unit includes a power harvesting module, a communication module, and one or more functional modules. The power harvesting module operable to produce a supply voltage from a received electromagnetic power signal (e.g., the electromagnetic signal 16 of FIGS. 1 and 2, the MRI signals of one or more the subsequent figures). The communication module and the at least one functional module are powered by the supply voltage.

In an example of operation, the communication device 24 (e.g., integrated into an MRI machine, a cellular telephone, a computer with a wireless interface, etc.) receives a downstream WAN signal from the network 42 via the WAN communication device 34. The downstream WAN signal may be generated by a remote monitoring device 36, a remote diagnostic device (e.g., computer 38 performing a remote diagnostic function), a remote control device (e.g., computer 38 performing a remote control function), and/or a medical record storage device (e.g., database 40).

The communication device 24 converts the downstream WAN signal into a downstream data signal. For example, the communication device 24 may convert the downstream WAN signal into a symbol stream in accordance with one or more wireless communication protocols (e.g., GSM, CDMA, WCDMA, HSUPA, HSDPA, WiMAX, EDGE, GPRS, IEEE 802.11, Bluetooth, ZigBee, universal mobile telecommunications system (UMTS), long term evolution (LTE), IEEE 802.16, evolution data optimized (EV-DO), etc.). The communication device 24 may convert the symbol stream into the downstream data signal using the same or a different wireless communication protocol.

Alternatively, the communication device 24 may convert the symbol stream into data that it interprets to determine how to structure the communication with the bio-medical unit 10 and/or what data (e.g., instructions, commands, digital information, etc.) to include in the downstream data signal. Having determined how to structure and what to include in the downstream data signal, the communication device 24 generates the downstream data signal in accordance with one or more wireless communication protocols. As yet another alternative, the communication device 24 may function as a relay, which provides the downstream WAN signal as the downstream data signal to the one or more bio-medical units 10.

When the communication device 24 has (and/or is processing) the downstream data signal to send to the bio-medical unit, it sets up a communication with the bio-medical unit. The set up may include identifying the particular bio-medical unit(s), determining the communication protocol used by the identified bio-medical unit(s), sending a signal to an electromagnetic device (e.g., MRI device, etc.) to request that it generates the electromagnetic power signal to power the bio-medical unit, and/or initiate a communication in accordance with the identified communication protocol. As an alternative to requesting a separate electromagnetic device to create the electromagnetic power signal, the communication device may include an electromagnetic device to create the electromagnetic power signal.

Having set up the communication, the communication device 24 wirelessly communicates the downstream data signal to the communication module of the bio-medical unit 10. The functional module of the bio-medical unit 10 processes the downstream data contained in the downstream data signal to perform a bio-medical functional, to store digital information contained in the downstream data, to administer a treatment (e.g., administer a medication, apply laser stimulus, apply electrical stimulus, etc.), to collect a sample (e.g., blood, tissue, cell, etc.), to perform a micro electro-mechanical function, and/or to collect data. For example, the bio-medical function may include capturing a digital image, capturing a radio frequency (e.g., 300 MHz to 300 GHz) radar image, an ultrasound image, a tissue sample, and/or a measurement (e.g., blood pressure, temperature, pulse, blood-oxygen level, blood sugar level, etc.).

When the downstream data requires a response, the functional module performs a bio-medical function to produce upstream data. The communication module converts the upstream data into an upstream data signal in accordance with the one or more wireless protocols. The communication device 24 converts the upstream data signal into an upstream wide area network (WAN) signal and transmits it to a remote diagnostic device, a remote control device, and/or a medical record storage device. In this manner, a person(s) operating the remote monitors 36 may view images and/or the data 30 gathered by the bio-medical units 10. This enables a specialist to be consulted without requiring the patient to travel to the specialist's office.

In another example of operation, one or more of the computers 38 may communicate with the bio-medical units 10 via the communication device 24, the WAN communication device 34, and the network 42. In this example, the computer 36 may provide commands 30 to one or more of the bio-medical units 10 to gather data, to dispense a medication, to move to a new position in the body, to perform a mechanical function (e.g., cut, grasp, drill, puncture, stitch, patch, etc.), etc. As such, the bio-medical units 10 may be remotely controlled via one or more of the computers 36.

In another example of operation, one or more of the bio-medical units 10 may read and/or write data from or to one or more of the databases 40. For example, data (e.g., a blood sample analysis) generated by one or more of the bio-medical units 10 may be written to one of the databases 40. The communication device 24 and/or one of the computers 36 may control the writing of data to or the reading of data from the database(s) 40. The data may further include medical records, medical images, prescriptions, etc.

Figure 6:
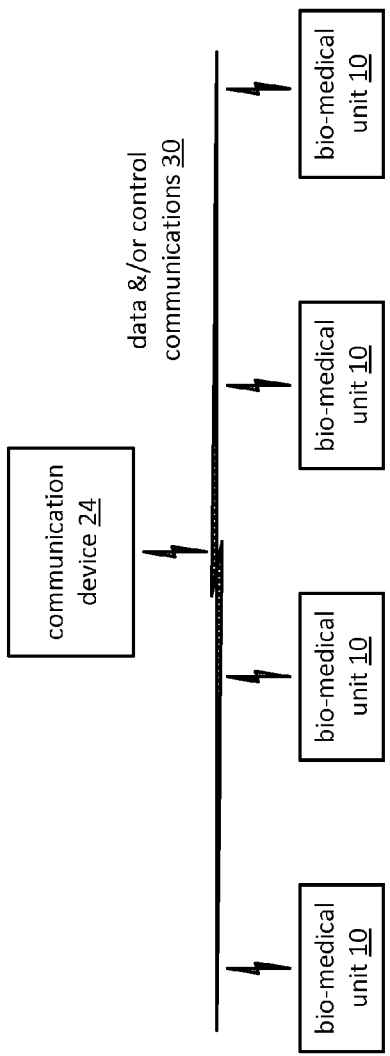
FIG. 6 is a diagram of another embodiment of a system in accordance with the present invention.

FIG. 6 is a diagram of another embodiment of a system that includes a plurality of bio-medical units 10. In this embodiment, the bio-medical units 10 can communicate with each other directly and/or communicate with the communication device 24 directly. The communication medium may be an infrared channel(s), an RF channel(s), a MMW channel(s), and/or ultrasound. The units may use a communication protocol such as token passing, carrier sense, time division multiplexing, code division multiplexing, frequency division multiplexing, etc.

Figure 7:
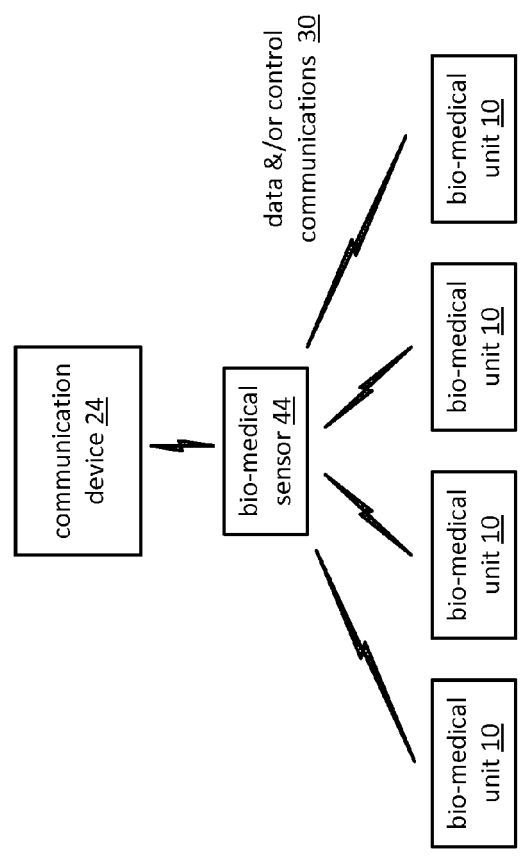
FIG. 7 is a diagram of another embodiment of a system in accordance with the present invention.

FIG. 7 is a diagram of another embodiment of a system that includes a plurality of bio-medical units 10. In this embodiment, one of the bio-medical units 44 functions as an access point for the other units. As such, the designated unit 44 routes communications between the units 10 and between one or more units 10 and the communication device 24. The communication medium may be an infrared channel(s), an RF channel(s), a MMW channel(s), and/or ultrasound. The units 10 may use a communication protocol such as token passing, carrier sense, time division multiplexing, code division multiplexing, frequency division multiplexing, etc.

Figure 8:
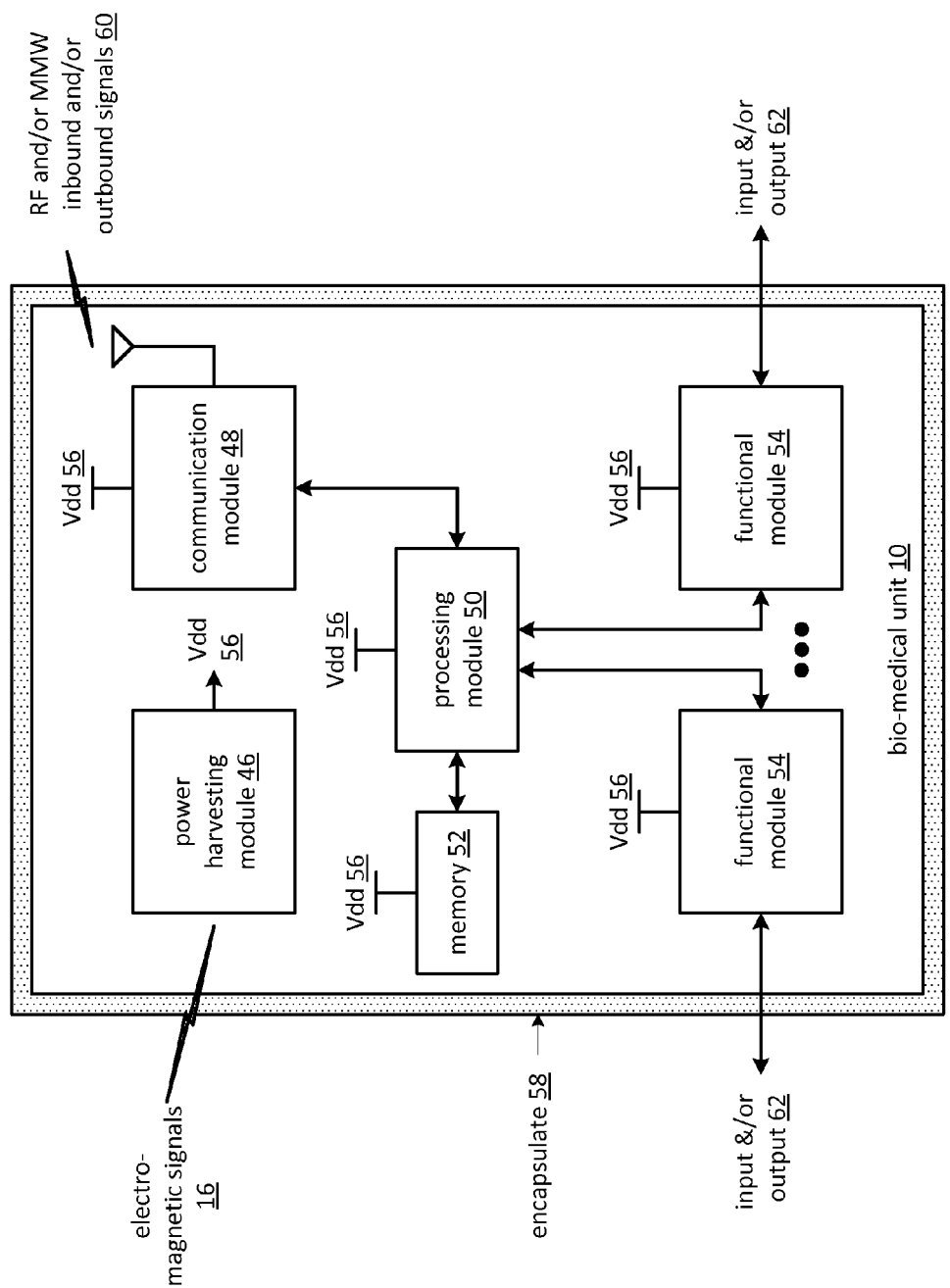
FIG. 8 is a schematic block diagram of an embodiment of a bio-medical unit in accordance with the present invention.

FIG. 8 is a schematic block diagram of an embodiment of a bio-medical unit 10 that includes a power harvesting module 46, a communication module 48, a processing module 50, memory 52, and one or more functional modules 54. The processing module 50 may be a single processing device or a plurality of processing devices. Such a processing device may be a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. The processing module 50 may have an associated memory 52 and/or memory element, which may be a single memory device, a plurality of memory devices, and/or embedded circuitry of the processing module. Such a memory device 52 may be a read-only memory, random access memory, volatile memory, non-volatile memory, static memory, dynamic memory, flash memory, cache memory, and/or any device that stores digital information. Note that if the processing module 50 includes more than one processing device, the processing devices may be centrally located (e.g., directly coupled together via a wired and/or wireless bus structure) or may be distributedly located (e.g., cloud computing via indirect coupling via a local area network and/or a wide area network). Further note that when the processing module 50 implements one or more of its functions via a state machine, analog circuitry, digital circuitry, and/or logic circuitry, the memory and/or memory element storing the corresponding operational instructions may be embedded within, or external to, the circuitry comprising the state machine, analog circuitry, digital circuitry, and/or logic circuitry. Still further note that, the memory element stores, and the processing module executes, hard coded and/or operational instructions corresponding to at least some of the steps and/or functions illustrated in FIGS. 1-23.

The power harvesting module 46 may generate one or more supply voltages 56 (Vdd) from a power source signal (e.g., one or more of MRI electromagnetic signals 16, magnetic fields 26, RF signals, MMW signals, ultrasound signals, light signals, and body motion). The power harvesting module 46 may be implemented as disclosed in U.S. Pat. No. 7,595,732 to generate one or more supply voltages from an RF signal. The power harvesting module 46 may be implemented as shown in one or more FIGS. 9-11 to generate one or more supply voltages 56 from an MRI signal 28 and/or magnetic field 26. The power harvesting module 46 may be implemented as shown in FIG. 12 to generate one or more supply voltage 56 from body motion. Regardless of how the power harvesting module generates the supply voltage(s), the supply voltage(s) are used to power the communication module 48, the processing module 50, the memory 52, and/or the functional modules 54.

In an example of operation, a receiver section of the communication module 48 receives an inbound wireless communication signal 60 and converts it into an inbound symbol stream. For example, the receiver section amplifies an inbound wireless (e.g., RF or MMW) signal 60 to produce an amplified inbound RF or MMW signal. The receiver section may then mix in-phase (I) and quadrature (Q) components of the amplified inbound RF or MMW signal with in-phase and quadrature components of a local oscillation to produce a mixed I signal and a mixed Q signal. The mixed I and Q signals are combined to produce an inbound symbol stream. In this embodiment, the inbound symbol may include phase information (e.g., $+/-\Delta\theta$ [phase shift] and/or $\theta(t)$ [phase modulation]) and/or frequency information (e.g., $+/-\Delta f$ [frequency shift] and/or $f(t)$ [frequency modulation]). In another embodiment and/or in furtherance of the preceding embodiment, the inbound RF or MMW signal includes amplitude information (e.g., $+/-\Delta A$ [amplitude shift] and/or $A(t)$ [amplitude modulation]). To recover the amplitude information, the receiver section includes an amplitude detector such as an envelope detector, a low pass filter, etc.

The processing module 50 converts the inbound symbol stream into inbound data and generates a command message based on the inbound data. The command message may instruction one or more of the functional modules to perform one or more electro-mechanical functions of gathering data, dispensing a medication, moving to a new position in the body, performing a mechanical function (e.g., cut, grasp, drill, puncture, stitch, patch, etc.), dispensing a treatment, collecting a biological sample, etc.

To convert the inbound symbol stream into the inbound data (e.g., voice, text, audio, video, graphics, etc.), the processing module 50 may perform one or more of: digital intermediate frequency to baseband conversion, time to frequency domain conversion, space-time-block decoding, space-frequency-block decoding, demodulation, frequency spread decoding, frequency hopping decoding, beamforming decoding, constellation demapping, deinterleaving, decoding, depuncturing, and/or descrambling. Such a conversion is typically prescribed by one or more wireless communication standards (e.g., GSM, CDMA, WCDMA, HSUPA, HSDPA, WiMAX, EDGE, GPRS, IEEE 802.11, Bluetooth, ZigBee, universal mobile telecommunications system (UMTS), long term evolution (LTE), IEEE 802.16, evolution data optimized (EV-DO), etc.).

The processing module 50 provides the command message to one or more of the micro-electromechanical functional modules 54. The functional module 54 performs an electro-mechanical function within a hosting body in accordance with the command message. Such an electro-mechanical function includes at least one of data gathering, motion, repairs, dispensing medication, biological sampling, diagnostics, applying laser treatment, applying ultrasound treatment, grasping, sawing, drilling, providing an electronic stimulus etc. Note that the functional modules 54 may be implemented using nanotechnology and/or microelectronic mechanical systems (MEMS) technology.

When requested per the command message (e.g. gather data and report the data), the micro electro-mechanical functional module 54 generates an electro-mechanical response based on the performing the electro-mechanical function. For example, the response may be data (e.g., heart rate, blood sugar levels, temperature, etc.), a biological sample (e.g., blood sample, tissue sample, etc.), acknowledgement of performing the function (e.g., acknowledge a software update, storing of data, etc.), and/or any appropriate response. The micro electro-mechanical functional module 54 provides the response to the processing module 50.

The processing module 50 converts the electro-mechanical response into an outbound symbol stream, which may be done in accordance with one or more wireless communication standards (e.g., GSM, CDMA, WCDMA, HSUPA, HSDPA, WiMAX, EDGE, GPRS, IEEE 802.11, Bluetooth, ZigBee, universal mobile telecommunications system (UMTS), long term evolution (LTE), IEEE 802.16, evolution data optimized (EV-DO), etc.). Such a conversion includes one or more of: scrambling, puncturing, encoding, interleaving, constellation mapping, modulation, frequency spreading, frequency hopping, beamforming, space-time-block encoding, space-frequency-block encoding, frequency to time domain conversion, and/or digital baseband to intermediate frequency conversion.

A transmitter section of the communication module 48 converts an outbound symbol stream into an outbound RF or MMW signal 60 that has a carrier frequency within a given frequency band (e.g., 900 MHz, 2.5 GHz, 5 GHz, 57-66 GHz, etc.). In an embodiment, this may be done by mixing the outbound symbol stream with a local oscillation to produce an up-converted signal. One or more power amplifiers and/or power amplifier drivers amplifies the up-converted signal, which may be RF or MMW bandpass filtered, to produce the outbound RF or MMW signal 60. In another embodiment, the transmitter section includes an oscillator that produces an oscillation. The outbound symbol stream provides phase information (e.g., $+/-\Delta\theta$ [phase shift] and/or $\theta(t)$ [phase modulation]) that adjusts the phase of the oscillation to produce a phase adjusted RF or MMW signal, which is transmitted as the outbound RF signal 60. In another embodiment, the outbound symbol stream includes amplitude information (e.g., $A(t)$ [amplitude modulation]), which is used to adjust the amplitude of the phase adjusted RF or MMW signal to produce the outbound RF or MMW signal 60.

In yet another embodiment, the transmitter section includes an oscillator that produces an oscillation. The outbound symbol provides frequency information (e.g., $+/-\Delta f$

[frequency shift] and/or f(t) [frequency modulation]) that adjusts the frequency of the oscillation to produce a frequency adjusted RF or MMW signal, which is transmitted as the outbound RF or MMW signal 60. In another embodiment, the outbound symbol stream includes amplitude information, which is used to adjust the amplitude of the frequency adjusted RF or MMW signal to produce the outbound RF or MMW signal 60. In a further embodiment, the transmitter section includes an oscillator that produces an oscillation. The outbound symbol provides amplitude information (e.g., +/−AA [amplitude shift] and/or A(t) [amplitude modulation]) that adjusts the amplitude of the oscillation to produce the outbound RF or MMW signal 60.

Note that the bio-medical unit 10 may be encapsulated by an encapsulate 58 that is non-toxic to the body. For example, the encapsulate 58 may be a silicon based product, a non-ferromagnetic metal alloy (e.g., stainless steel), etc. As another example, the encapsulate 58 may include a spherical shape and have a ferromagnetic liner that shields the unit from a magnetic field and to offset the forces of the magnetic field. Further note that the bio-medical unit 10 may be implemented on a single die that has an area of a few millimeters or less. The die may be fabricated in accordance with CMOS technology, Gallium-Arsenide technology, and/or any other integrated circuit die fabrication process.

Figure 9:
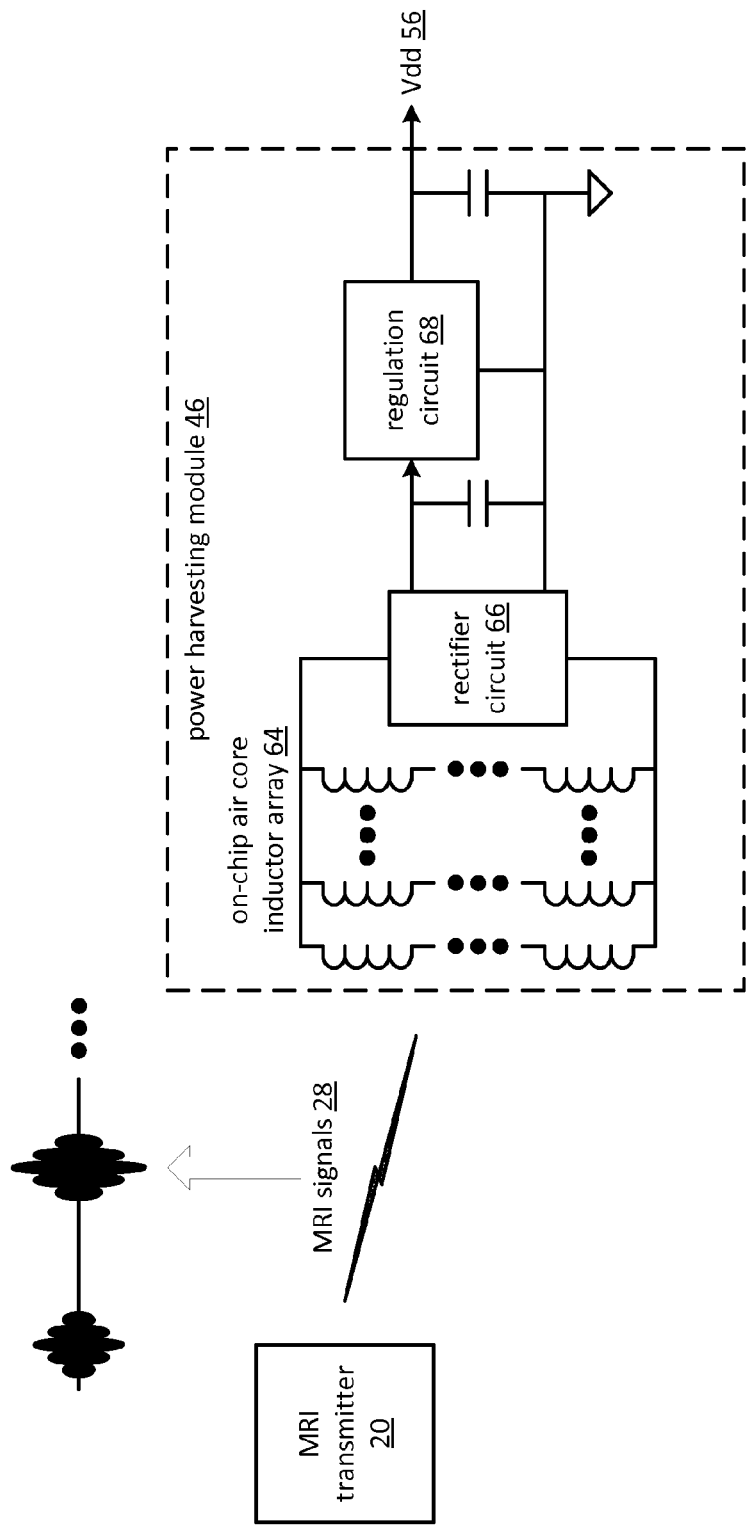
FIG. 9 is a schematic block diagram of an embodiment of a power harvesting module in accordance with the present invention.

FIG. 9 is a schematic block diagram of an embodiment of a power harvesting module 46 that includes an array of on-chip air core inductors 64, a rectifying circuit 66, capacitors, and a regulation circuit 68. The inductors 64 may each having an inductance of a few nano-Henries to a few micro-Henries and may be coupled in series, in parallel, or a series parallel combination.

In an example of operation, the MRI transmitter 20 transmits MRI signals 28 at a frequency of 3-45 MHz at a power level of up to 35 KWatts. The air core inductors 64 are electromagnetically coupled to generate a voltage from the magnetic and/or electric field generated by the MRI signals 28. Alternatively or in addition to, the air core inductors 64 may generate a voltage from the magnetic field 26 and changes thereof produced by the gradient coils. The rectifying circuit 66 rectifies the AC voltage produced by the inductors to produce a first DC voltage. The regulation circuit generates one or more desired supply voltages 56 from the first DC voltage.

The inductors 64 may be implemented on one more metal layers of the die and include one or more turns per layer. Note that trace thickness, trace length, and other physical properties affect the resulting inductance.

Figure 10:
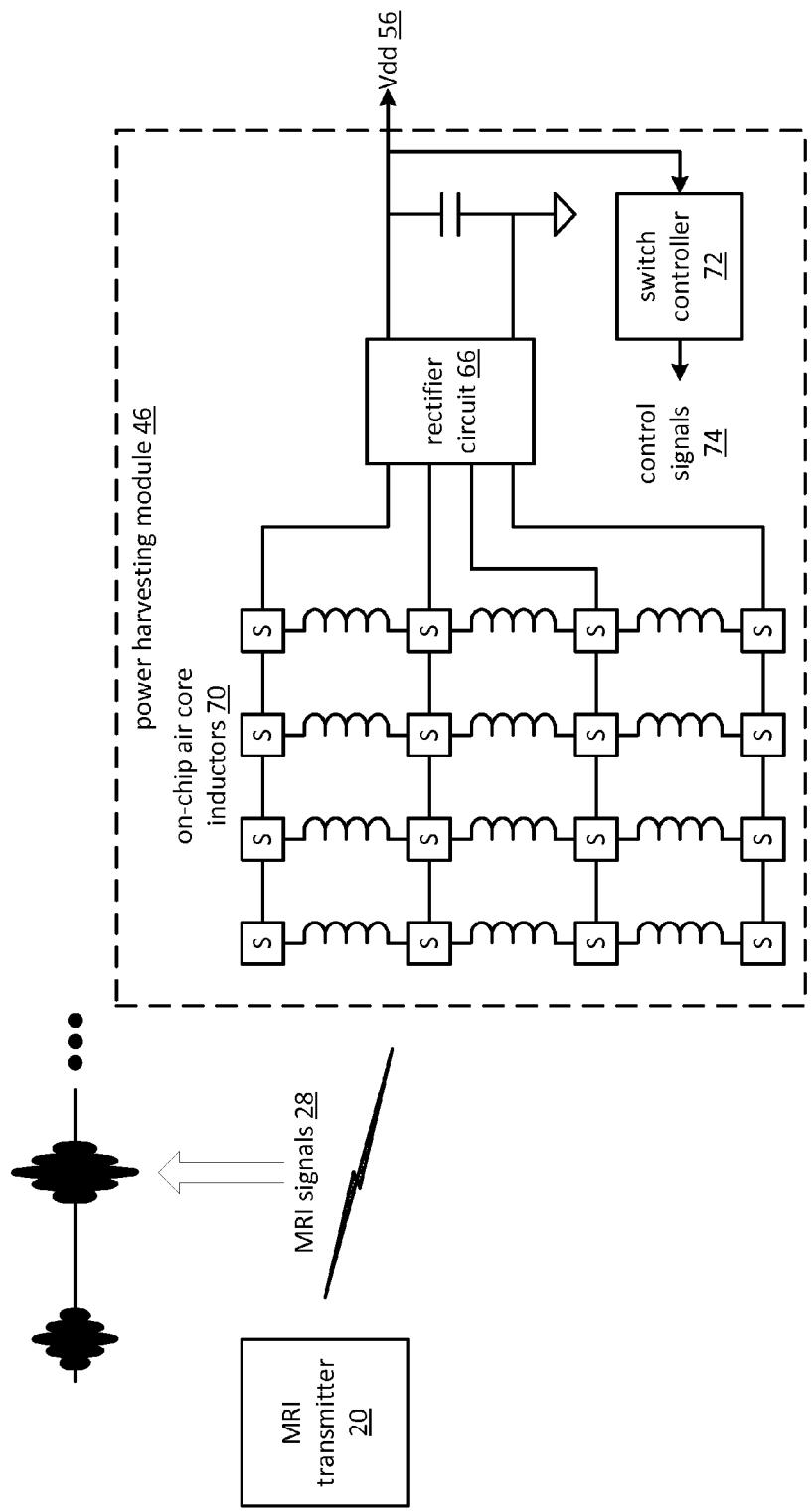
FIG. 10 is a schematic block diagram of another embodiment of a power harvesting module in accordance with the present invention.

FIG. 10 is a schematic block diagram of another embodiment of a power harvesting module 46 that includes a plurality of on-chip air core inductors 70, a plurality of switching units (S), a rectifying circuit 66, a capacitor, and a switch controller 72. The inductors 70 may each having an inductance of a few nano-Henries to a few micro-Henries and may be coupled in series, in parallel, or a series parallel combination.

In an example of operation, the MRI transmitter 20 transmits MRI signals 28 at a frequency of 3-45 MHz at a power level of up to 35 KWatts. The air core inductors 70 are electromagnetically coupled to generate a voltage from the magnetic and/or electric field generated by the MRI signals 28. The switching module 72 engages the switches via control signals 74 to couple the inductors 70 in series and/or parallel to generate a desired AC voltage. The rectifier circuit 66 and the capacitor(s) convert the desired AC voltage into the one or more supply voltages 56.

Figure 11:
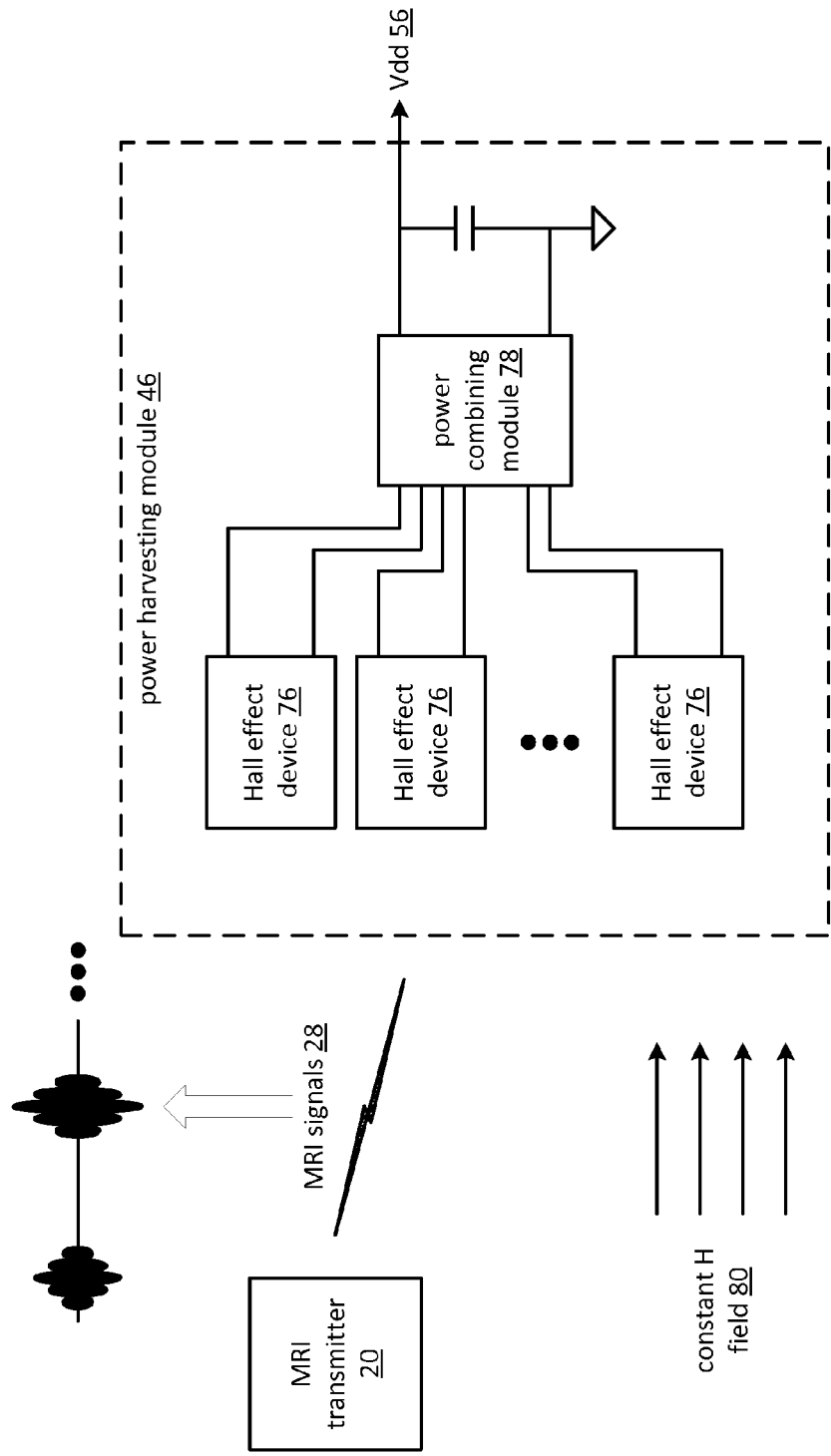
FIG. 11 is a schematic block diagram of another embodiment of a power harvesting module in accordance with the present invention.
Figure 12:
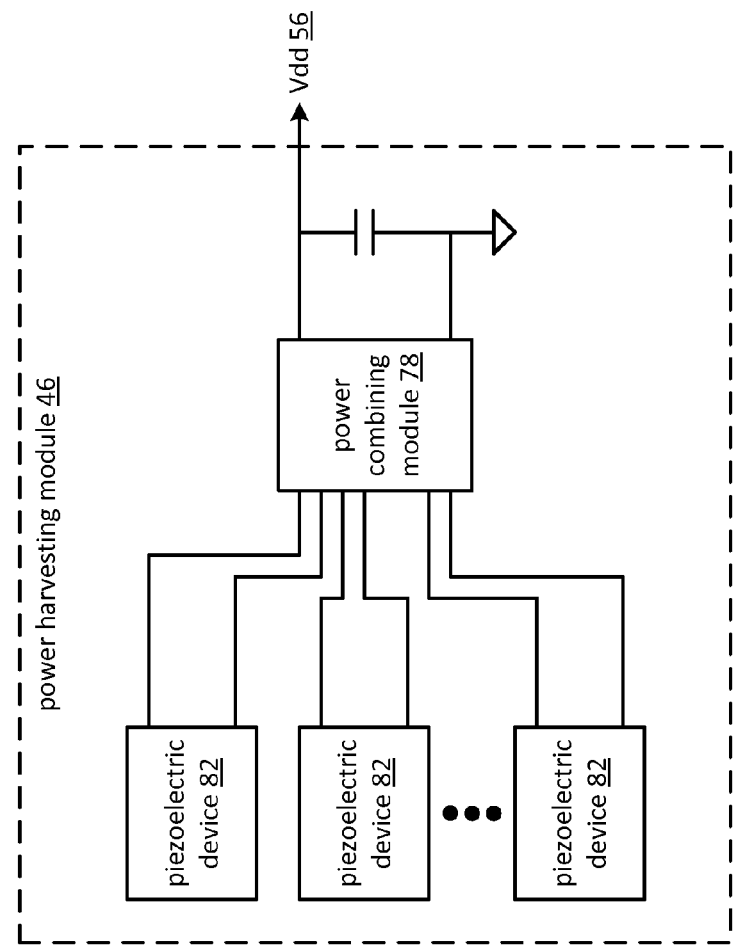
FIG. 12 is a schematic block diagram of another embodiment of a power harvesting module in accordance with the present invention.

FIG. 11 is a schematic block diagram of another embodiment of a power harvesting module 46 that includes a plurality of Hall effect devices 76, a power combining module 78, and a capacitor(s). In an example of operation, the Hall effect devices 76 generate a voltage based on the constant magnetic field (H) and/or a varying magnetic field. The power combining module 78 (e.g., a wire, a switch network, a transistor network, a diode network, etc.) combines the voltages of the Hall effect devices 76 to produce the one or more supply voltages 56.

FIG. 12 is a schematic block diagram of another embodiment of a power harvesting module 46 that includes a plurality of piezoelectric devices 82, a power combining module 78, and a capacitor(s). In an example of operation, the piezoelectric devices 82 generate a voltage based on body movement, ultrasound signals, movement of body fluids, etc. The power combining module 78 (e.g., a wire, a switch network, a transistor network, a diode network, etc.) combines the voltages of the Hall effect devices 82 to produce the one or more supply voltages 56. Note that the piezoelectric devices 82 may include one or more of a piezoelectric motor, a piezoelectric actuator, a piezoelectric sensor, and/or a piezoelectric high voltage device.

The various embodiments of the power harvesting module 46 may be combined to generate more power, more supply voltages, etc. For example, the embodiment of FIG. 9 may be combined with one or more of the embodiments of FIGS. 11 and 12.

Figure 13:
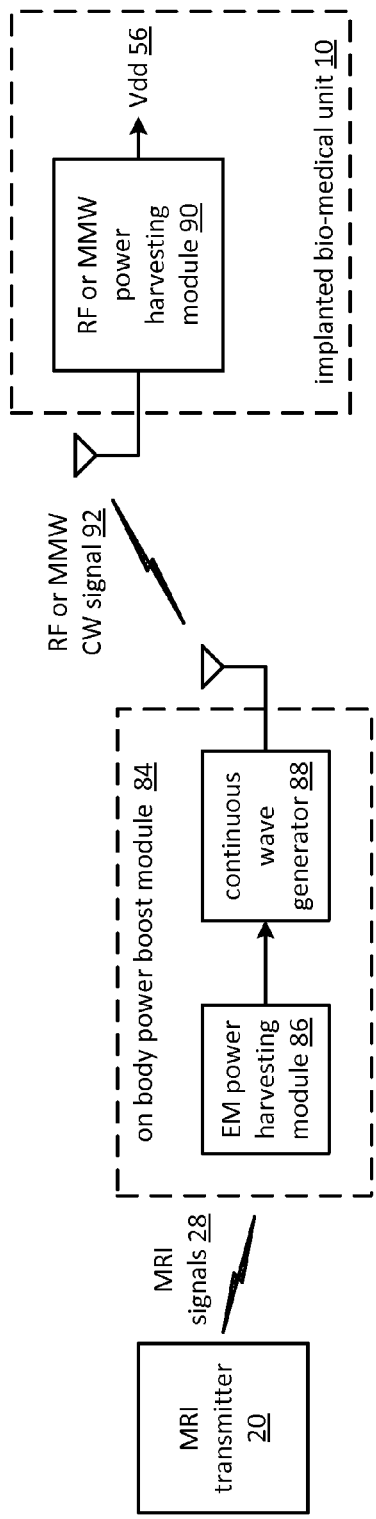
FIG. 13 is a schematic block diagram of an embodiment of a power boost module in accordance with the present invention.

FIG. 13 is a schematic block diagram of an embodiment of a power boost module 84 that harvests energy from MRI signals 28 and converts the energy into continuous wave (CW) RF (e.g., up to 3 GHz) and/or MMW (e.g., up to 300 GHz) signals 92 to provide power to the implanted bio-medical units 10. The power boost module 84 sits on the body of the person under test or treatment and includes an electromagnetic power harvesting module 86 and a continuous wave generator 88. In such an embodiment, the power boosting module 84 can recover significantly more energy than a bio-medical unit 10 since it can be significantly larger. For example, a bio-medical unit 10 may have an area of a few millimeters squared while the power boosting module 84 may have an area of a few to tens of centimeters squared.

Figure 14:
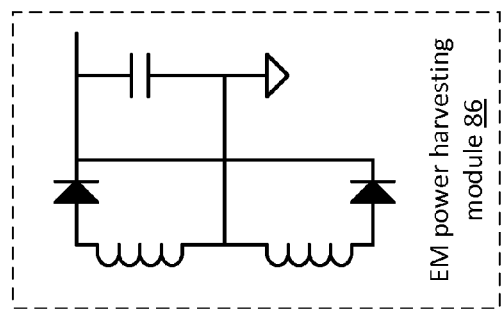
FIG. 14 is a schematic block diagram of an embodiment of an electromagnetic (EM)) power harvesting module in accordance with the present invention.

FIG. 14 is a schematic block diagram of an embodiment of an electromagnetic (EM)) power harvesting module 86 that includes inductors, diodes (or transistors) and a capacitor. The inductors may each be a few mili-Henries such that the power boost module can deliver up to 10's of mili-watts of power.

Figure 15:
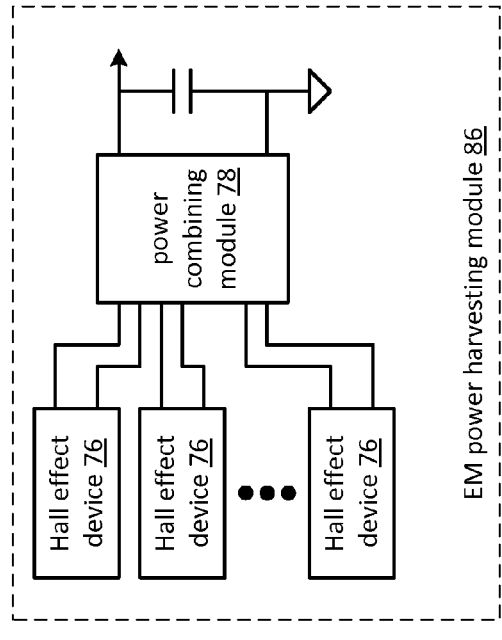
FIG. 15 is a schematic block diagram of another embodiment of an electromagnetic (EM)) power harvesting module in accordance with the present invention.

FIG. 15 is a schematic block diagram of another embodiment of an electromagnetic (EM)) power harvesting module 86 that includes a plurality of Hall effect devices 76, a power combining module 78, and a capacitor. This functions as described with reference to FIG. 11, but the Hall effect devices 76 can be larger such that more power can be produced. Note that the EM power harvesting module 86 may include a combination of the embodiment of FIG. 14 and the embodiment of FIG. 15.

Figure 16:
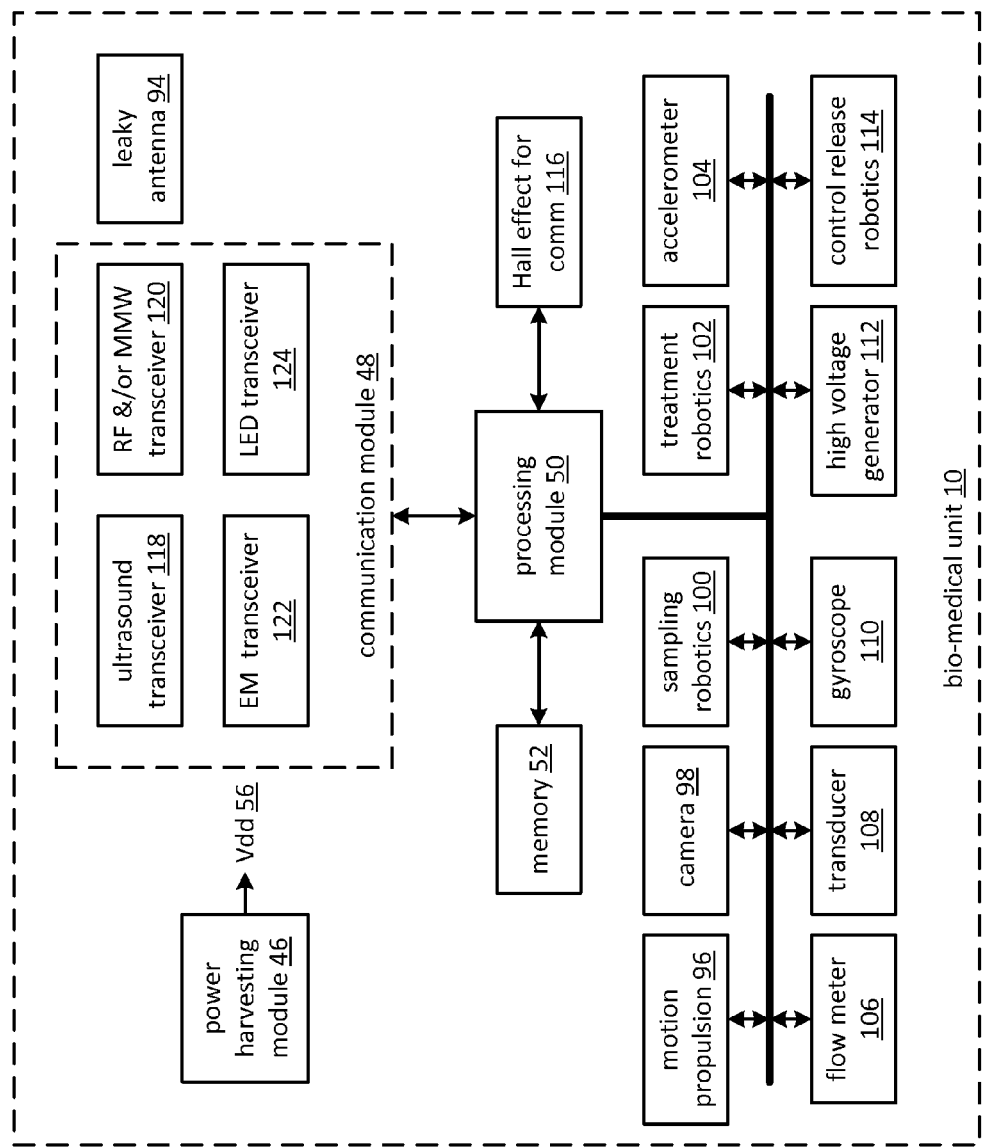
FIG. 16 is a schematic block diagram of another embodiment of a bio-medical unit in accordance with the present invention.

FIG. 16 is a schematic block diagram of another embodiment of a bio-medical unit 10 that includes a power harvesting module 46, a communication module 48, a processing module 50, memory 52, and may include one or more functional modules 54 and/or a Hall effect communication module 116. The communication module 48 may include one or more of an ultrasound transceiver 118, an electromagnetic transceiver 122, an RF and/or MMW transceiver 120, and a light source (LED) transceiver 124. Note that examples of the various types of communication modules 48 will be described in greater detail with reference to one or more of FIGS. 17-23.

The one or more functional modules 54 may perform a repair function, an imaging function, and/or a leakage detection function, which may utilize one or more of a motion propulsion module 96, a camera module 98, a sampling robotics module 100, a treatment robotics module 102, an accelerometer module 104, a flow meter module 106, a transducer module 108, a gyroscope module 110, a high voltage generator module 112, a control release robotics module 114, and/or other functional modules described with reference to one or more other figures. The functional modules 54 may be implemented using MEMS technology and/or nanotechnology. For example, the camera module 98 may be implemented as a digital image sensor in MEMS technology.

The Hall effect communication module 116 utilizes variations in the magnetic field and/or electrical field to produce a plus or minus voltage, which can be encoded to convey information. For example, the charge applied to one or more Hall effect devices 76 may be varied to produce the voltage change. As another example, an MRI transmitter 20 and/or gradient unit may modulate a signal on the magnetic field 26 it generates to produce variations in the magnetic field 26.

Figure 17:
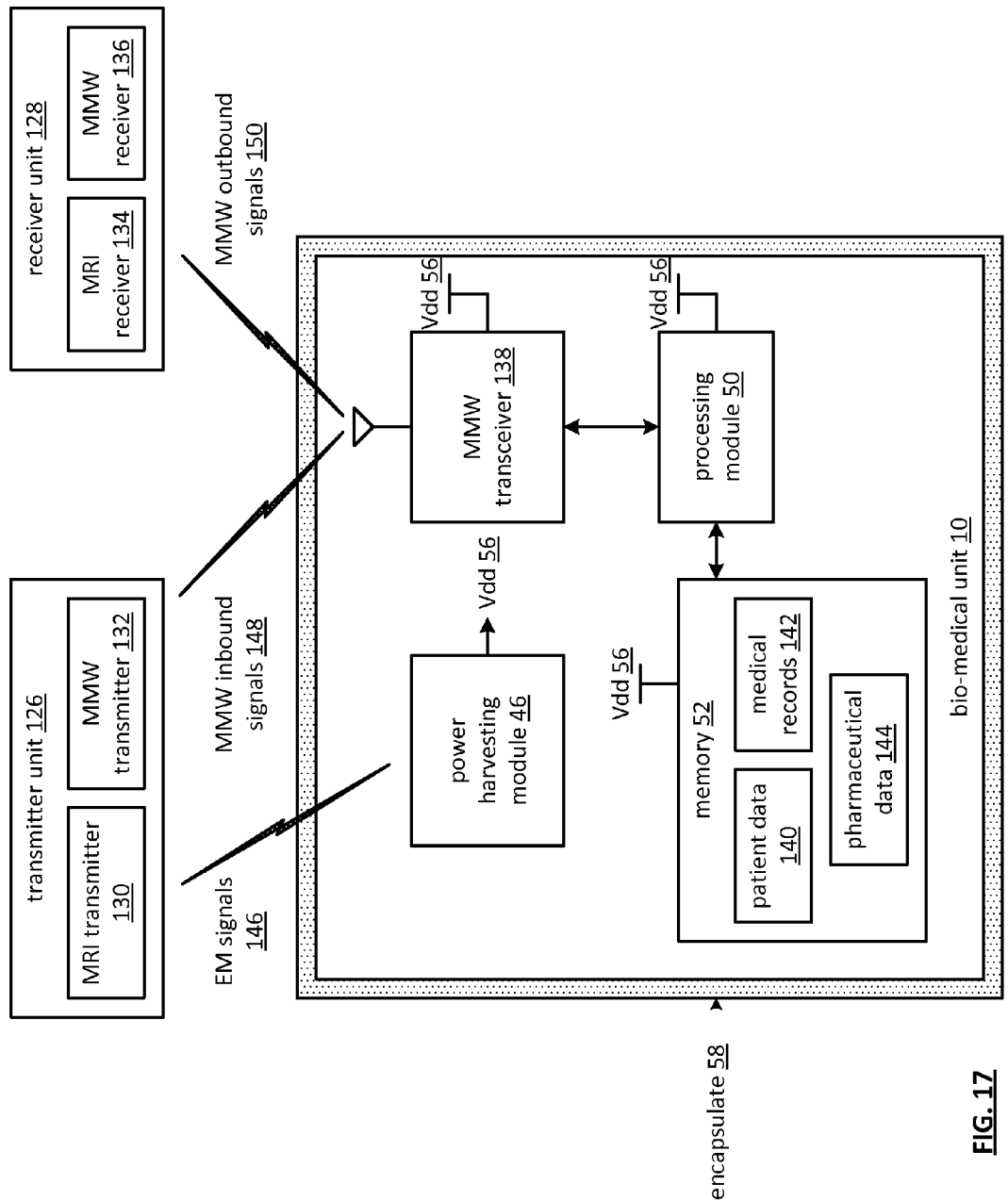
FIG. 17 is a diagram of another embodiment of a system in accordance with the present invention.

FIG. 17 is a diagram of another embodiment of a system that includes one or more bio-medical units 10, a transmitter unit 126, and a receiver unit 128. Each of the bio-medical units 10 includes a power harvesting module 46, a MMW transceiver 138, a processing module 50, and memory 52. The transmitter unit 126 includes a MRI transmitter 130 and a MMW transmitter 132. The receiver unit 128 includes a MRI receiver 134 and a MMW receiver 136. Note that the MMW transmitter 132 and MMW receiver 136 may be in the same unit (e.g., in the transmitter unit, in the receiver unit, or housed in a separate device).

In an example of operation, the bio-medical unit 10 recovers power from the electromagnetic (EM) signals 146 transmitted by the MRI transmitter 130 and communicates via MMW signals 148-150 with the MMW transmitter 132 and MMW receiver 136. The MRI transmitter 130 may be part of a portable MRI device, may be part of a full sized MRI machine, and/or part of a separate device for generating EM signals 146 for powering the bio-medical unit 10.

Figure 18:
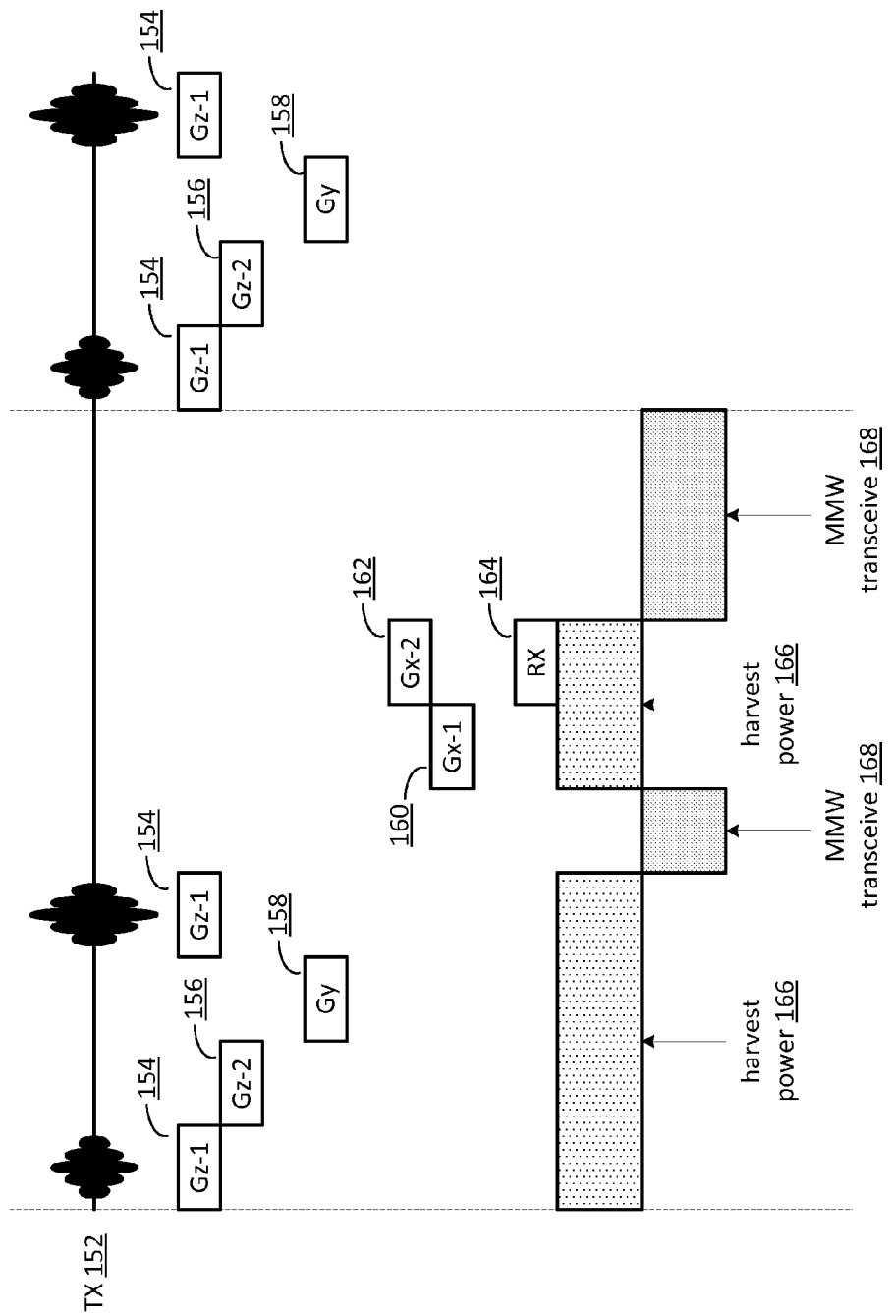
FIG. 18 is a diagram of an example of a communication protocol within a system in accordance with the present invention.

FIG. 18 is a diagram of an example of a communication protocol within the system of FIG. 17. In this diagram, the MRI transmitter 20 transmits RF signals 152, which have a frequency in the range of 3-45 MHz, at various intervals with varying signal strengths. The power harvesting module 46 of the bio-medical units 10 may use these signals to generate power for the bio-medical unit 10.

In addition to the MRI transmitter 20 transmitting its signal, a constant magnetic field and various gradient magnetic fields 154-164 are created (one or more in the x dimension Gx, one or more in the y dimension Gy, and one or more in the z direction Gz). The power harvesting module 46 of the bio-medical unit 10 may further use the constant magnetic field and/or the varying magnetic fields 154-164 to create power for the bio-medical unit 10.

During non-transmission periods of the cycle, the bio-medical unit 10 may communicate 168 with the MMW transmitter 132 and/or MMW receiver 136. In this regard, the bio-medical unit 10 alternates from generating power to MMW communication in accordance with the conventional transmission-magnetic field pattern of an MRI machine.

Figure 19:
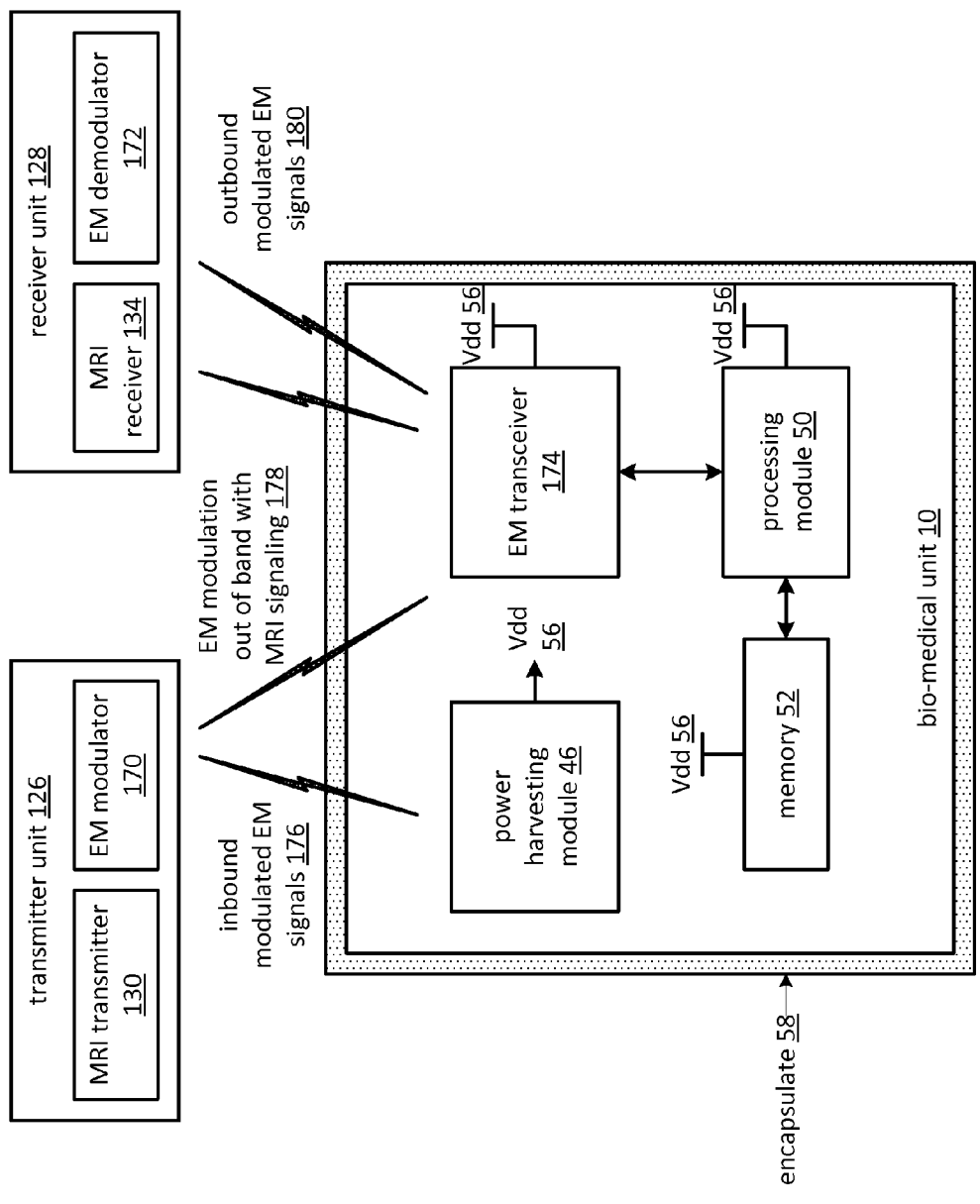
FIG. 19 is a diagram of another embodiment of a system in accordance with the present invention.

FIG. 19 is a diagram of another embodiment of a system includes one or more bio-medical units 10, a transmitter unit 126, and a receiver unit 128. Each of the bio-medical units 10 includes a power harvesting module 46, an EM transceiver 174, a processing module 50, and memory 52. The transmitter unit 126 includes a MRI transmitter 130 and electromagnetic (EM) modulator 170. The receiver unit 128 includes a MRI receiver 134 and a EM demodulator 172. The transmitter unit 126 and receiver unit 128 may be part of a portable MRI device, may be part of a full sized MRI machine, or part of a separate device for generating EM signals for powering the bio-medical unit 10.

In an example of operation, the MRI transmitter 130 generates an electromagnetic signal that is received by the EM modulator 170. The EM modulator 170 modulates a communication signal on the EM signal to produce an inbound modulated EM signal 176. The EM modulator 170 may modulate (e.g., amplitude modulation, frequency modulation, amplitude shift keying, frequency shift keying, etc.) the magnetic field and/or electric field of the EM signal. In another embodiment, the EM modulator 170 may modulate the magnetic fields produced by the gradient coils to produce the inbound modulated EM signals 176.

The bio-medical unit 10 recovers power from the modulated electromagnetic (EM) signals. In addition, the EM transceiver 174 demodulates the modulated EM signals 178 to recover the communication signal. For outbound signals, the EM transceiver 174 modulates an outbound communication signal to produce outbound modulated EM signals 180. In this instance, the EM transceiver 174 is generating an EM signal that, in air, is modulated on the EM signal transmitted by the transmitter unit 126. In one embodiment, the communication in this system is half duplex such that the modulation of the inbound and outbound communication signals is at the same frequency. In another embodiment, the modulation of the inbound and outbound communication signals are at different frequencies to enable full duplex communication.

Figure 20:
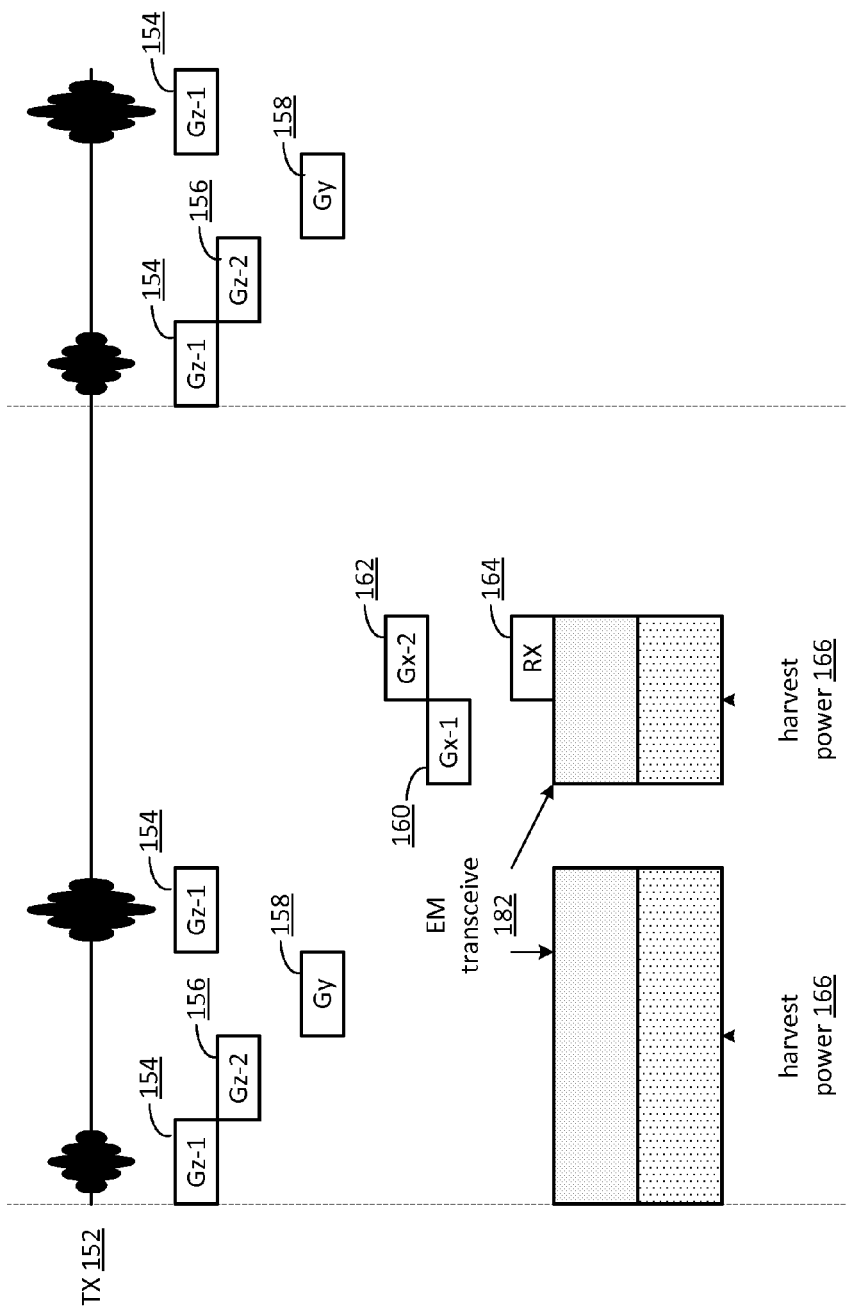
FIG. 20 is a diagram of another example of a communication protocol within a system in accordance with the present invention.

FIG. 20 is a diagram of another example of a communication protocol within the system of FIG. 19. In this diagram, the MRI transmitter 20 transmits RF signals 152, which have a frequency in the range of 3-45 MHz, at various intervals with varying signal strengths. The power harvesting module 46 of the bio-medical units 10 may use these signals to generate power for the bio-medical unit 10.

In addition to the MRI transmitter 20 transmitting its signal, a constant magnetic field and various gradient magnetic fields are created 154-164 (one or more in the x dimension Gx, one or more in the y dimension Gy, and one or more in the z direction Gz). The power harvesting module 46 of the bio-medical unit 10 may further use the constant magnetic field and/or the varying magnetic fields 154-164 to create power for the bio-medical unit 10.

During the transmission periods of the cycle, the bio-medical unit 10 may communicate via the modulated EM signals 182. In this regard, the bio-medical unit 10 generates power and communicates in accordance with the conventional transmission-magnetic field pattern of an MRI machine.

Figure 21:
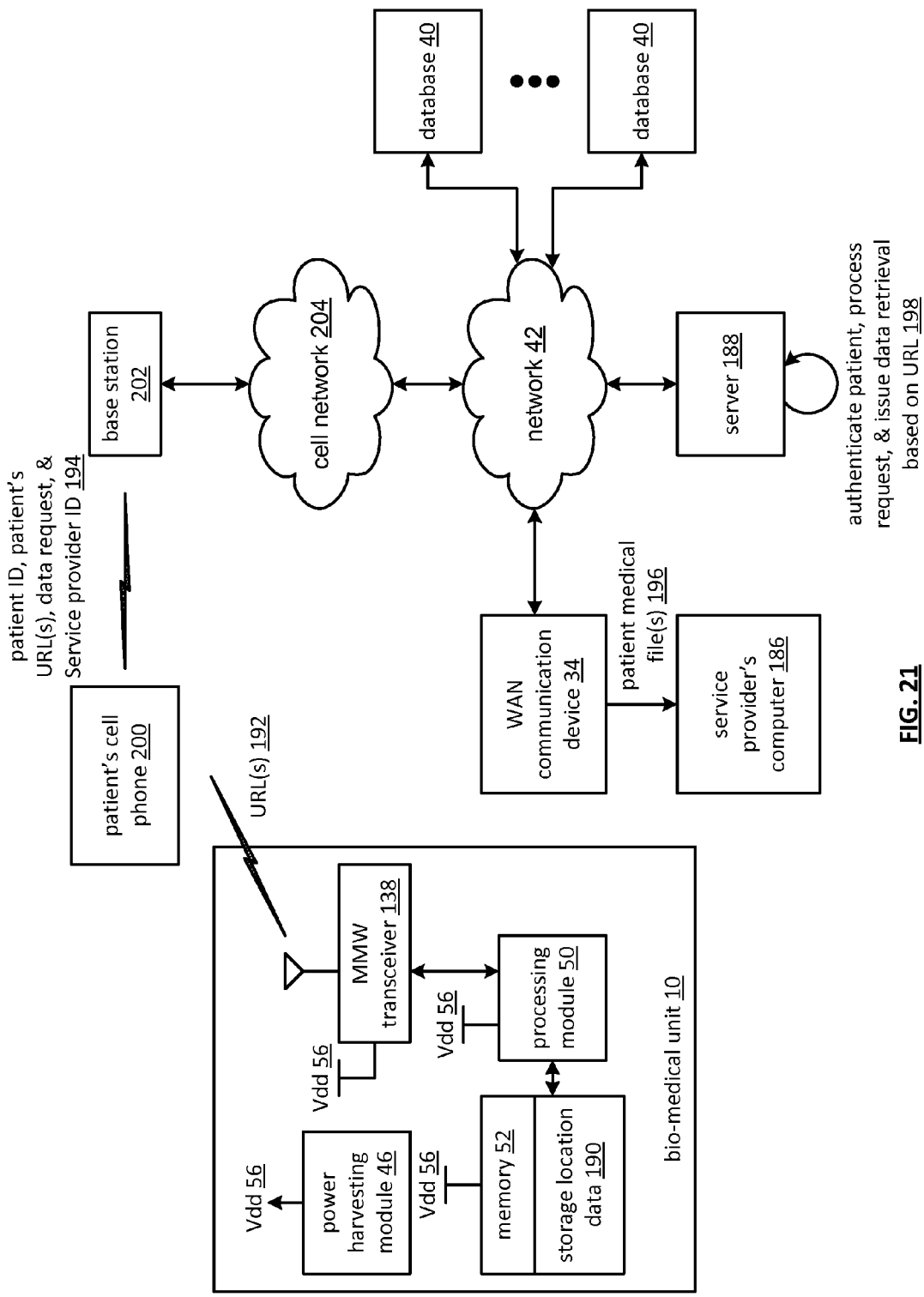
FIG. 21 is a diagram of an embodiment of a bio-medical unit collecting audio and/or ultrasound data in accordance with the present invention.

FIG. 21 is a diagram of another embodiment of a system that includes one or more bio-medical units 10, a service provider's communication device 184, a WAN communication device 34, a service provider's computer 186, a network 42, one or more databases 40, and a server 188. The bio-medical unit 10 includes a power harvesting module 46, a processing module 50, memory 52, and a MMW transceiver 138. The memory 52 stores patient data storage location information 190 (e.g., a local area network address; a wide area network address; a web page address; and/or a uniform resource locator (URL)) for a patient (i.e., the person in which or on which the bio-medical unit 10 is implanted, affixed, or affiliated with via a medical tag, key chain, etc).

In an example of operation, a patient's medical history may be stored in a plurality of different locations. For example, a patient's primary physician has one set of records for the patient; each hospital stay of the patient has different medical records; drugs stores have various pharmaceutical records for the patient; and the patient may change primary physicians, hospitals, and or drugstores used several times throughout their lifetime. As such, a patient's medical history is generally scattered among a plurality of doctors' offices, hospitals, drug stores, etc.

The biomedical unit 10 stores storage location data 190 that points to the plurality of locations storing the patient's total medical history. Each visit to the patient's primary physician is recorded in the physician's records and a corresponding entry is stored in the memory 52 of the biomedical unit 10. Similarly, each visit to a hospital is recorded in the hospital's records and a corresponding data storage location entry is stored in memory 52; and each prescription filled by a drugstore is recorded in the drugstores records and a corresponding data storage location entry is stored in memory 52.

In addition to updating the storage location data 194 each doctor visit, hospital visit, and/or pharmaceutical prescription, an authorized service provider (e.g., the patient's primary physician, an emergency room doctor, a pharmacist, an emergency medical technician, etc.) may retrieve at least a portion of the patient's medical record history. For example, the patient's primary physician may remotely access the patient's medical history via its service provider computer 186. In this instance, the service provider's computer 186 transmits a request to the patient's cell phone 200 to retrieve particular storage location data regarding a particular medical matter.

Upon receiving the request, the cellular telephone 200 transmits a request to the transceiver 138 of the biomedical unit 10. The request is transmitted as a wireless communication in the radio frequency band and or the millimeter wave (MMW) frequency band. The transceiver 138 converts the inbound wireless signal into an inbound signal and provides it to the processing module 50. Such a conversion process was previously discussed with reference to FIG. 8.

The processing module 50 converts the inbound signal into a request for storage location information of a specific medical matter (e.g., image data of at least a portion of the host body (x-ray, MRI, CAT scan, etc.); information regarding identity of the host body (i.e., the patient identity); current and/or past medication prescriptions for patient; physical examination data of the patient; operations performed on the patient; and/or blood test results of the patient). The processing module then retrieves the storage location information for the specific medical matter from memory based on the request. Next, the processing module 50 converts the storage location information for the specific medical matter into an outbound signal.

The transceiver 138 convert the outbound signal into an outbound wireless signal, which it transmits to the cellular telephone 200. The cellular telephone 200 provides the storage location information for a specific metal matter to the service provider's computer 180 via the cellular network 204 and/or the wide area network 42.

In furtherance of the preceding example or as an alternative to the preceding example, after the processing module has converted the inbound signal into the request for storage location information of the specific medical matter, it then seeks to determine the identity of the source of the request and to verify that the source is authorized to access the storage location information for this specific medical matter. For example, when the source of the request is the patient's cellular telephone 200, which already has established an affiliation with the biomedical unit, the biomedical unit authenticates the cellular telephone 200 and processes the request as previously discussed.

When the source of the request is a service provider communication device, the processing module executes an authentication process to authenticate the service provider communication device. For example, the processing module sends an authentication request to server 188 via the patient's cell phone 200. The server 188 (which may be operated by an independent medical security entity, a home computer of the patient, a secure computer of the patient's primary physician, etc.) processes 198 the request. If the service provider is authenticated and the request is valid, the server 188 issues authentication message, which is provided to the biomedical unit 10. Upon receiving the authentication message, the processing module retrieves the storage location information for the specific medical matter from memory and provides it, via the transceiver 138, to the patient's cellular telephone 200.

The cellular telephone 200 provide the storage location information to the service provider's computer 186, which utilizes the storage location information to retrieve the data concerning the specific medical matter. For example, the storage location information may correspond to a URL of a record in one of the databases 40. In this instance, the service provider's computer sends a retrieval message to one of the databases using the URL to retrieve the record regarding the specific medical matter.

In furtherance of the preceding example and/or as an alternative example, the storage location information 190 may be updated on a per medical matter basis. For example, when the patient (i.e., the host body) visits his/her primary physician, a new medical matter is established. In this instance, the processing module communicates, via the transceiver 138, with an external device regarding the medical matter. During the communication with the external device (e.g., the cellular telephone 200), the processing module obtains (e.g., receives, determines, looks up, etc.) storage location information regarding the medical matter. The processing module then aggregates the storage location information with patient data storage location information to produce updated patient data storage location information 190.

As a more specific example, the processing module generates a communication initiation message to initiate the communication with a service provider communication device (e.g., the primary physician's computer). The transceiver converts the communication initiation message into an outbound wireless signal, which it transmits to the service provider's computer 186 directly or via its cellular telephone 200. In response to the communication initiation message, the service provider's computer 186 generates a communication response message, which indicates its intent to establish the communication and includes its identification information.

The transceiver receives an inbound wireless signal representative of the communication response message, which it converts into the communication response message. The processing module processes the communication response message to verify authenticity of the service provider communication device and, when the authenticity of the service provider is verified, it allows reception of the storage location information.

To facilitate the storage and/or retrieval of the storage location data 190 from the bio-medical unit 10, the cellular telephone 200 includes an algorithm that begins by establishing a wireless communication link with a bio-medical unit. The algorithm continues by transmitting, via the wireless communication link, a command (e.g., a retrieval command or a storage command) regarding a specific medical matter of a host body associated to the bio-medical unit.

The algorithm continues, when the command is a retrieval command, by including in the command a request for storage location information for the specific medical matter. The algorithm continues by receiving, via the wireless communication link, the storage location information. The algorithm continues by initiating a cellular telephone communication to retrieve data regarding the specific medical matter based on the storage location information.

When the command is a storage command, the algorithm continues by including in the command an instruction to store the storage location information for the specific medical matter. In this instance, the algorithm may further include receiving a download instruction from a remote medical device via a cellular telephone communication and, in response to the download instruction, generating the storage command.

Figure 22:
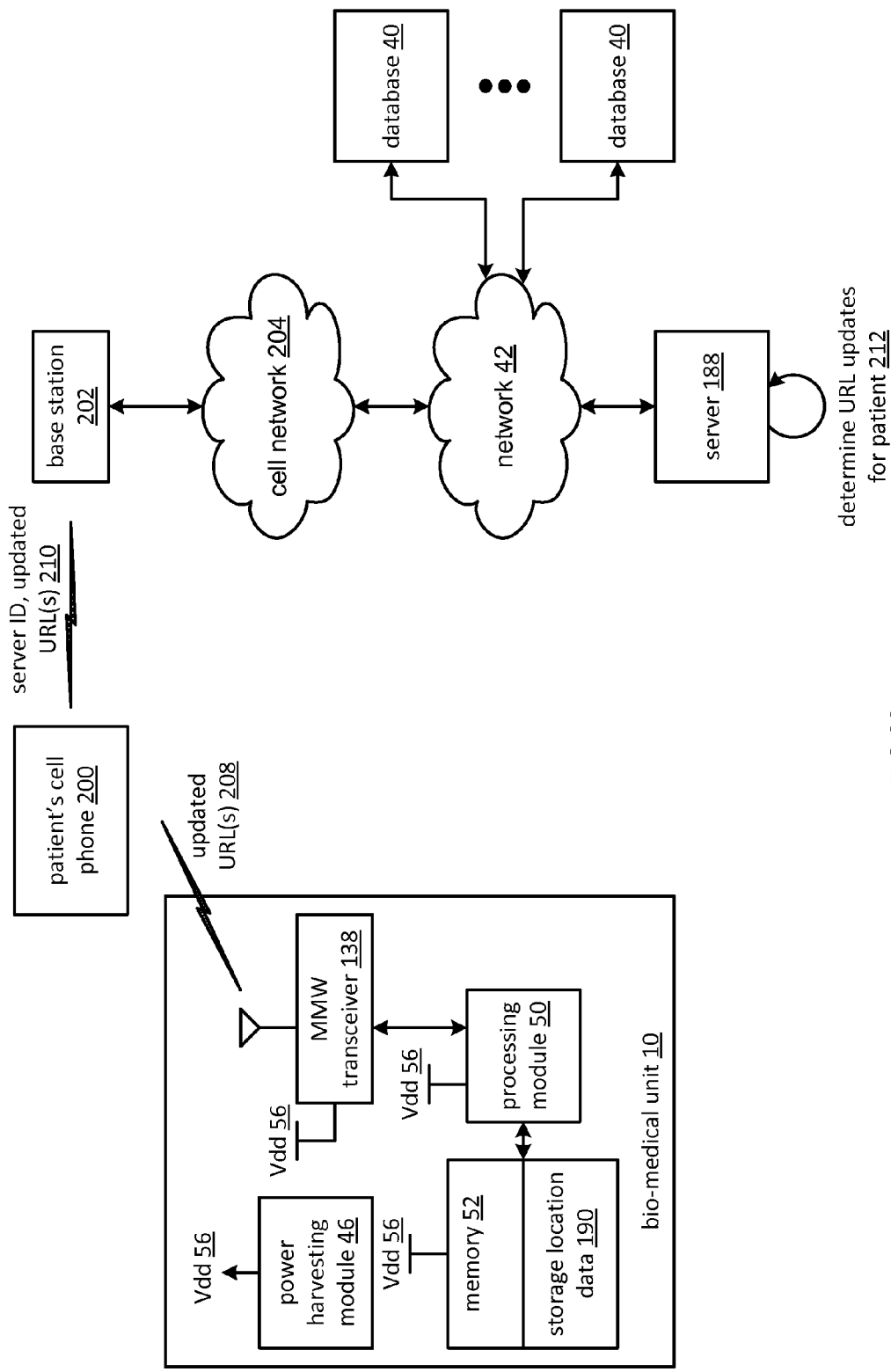
FIG. 22 is a diagram of another embodiment of a network of bio-medical units communicating via audio and/or ultrasound signaling in accordance with the present invention.

FIG. 22 is a diagram of another embodiment of a system that includes one or more bio-medical units 10, the patient's cell phone 200, a WAN communication device 34, a service provider's computer 186, a network 42, one or more databases 40, and a server 188. The bio-medical unit 10 includes a power harvesting module 46, a processing module 50, memory 52, and a MMW transceiver 138. The memory 52 is storing storage location data 190 for the patient. Note that the bio-medical unit 10 may be implanted in the patient, on the patient's body, or on the patient's person (e.g., in a medical tag, a key chain, etc.).

The data 190 may include one or more URLs 192 that identify locations of the patient's medical records. For example, one URL may be for the patient's prescription records, another may be for hospitalizations, another for general office visits, etc. In this regard, the bio-medical unit 10 is an index to easily access the patient's medical history.

For a service provider to access the patient's medical records, or a portion thereof, the patient's cell phone retrieves 200 the URL(s) 192 from the bio-medical unit 10. This may be done as previously discussed. The cell phone 200 generates a request to access the patient's information, where the request includes the URL(s) 192, the service provider's ID, the patient's ID, and a data request. The request is provided, via the WAN device 34 and the network 42, to the server 188.

The server 188 processes 198 the request. If the service provider is authenticated and the request is valid, the server issues a data retrieval message to the one or more databases 40 identified by the URL(s) 192. The addressed database(s) 40 retrieves the data and provides it via the network 42 and the WAN device 34 to the service provider's computer 186.

Figure 23:
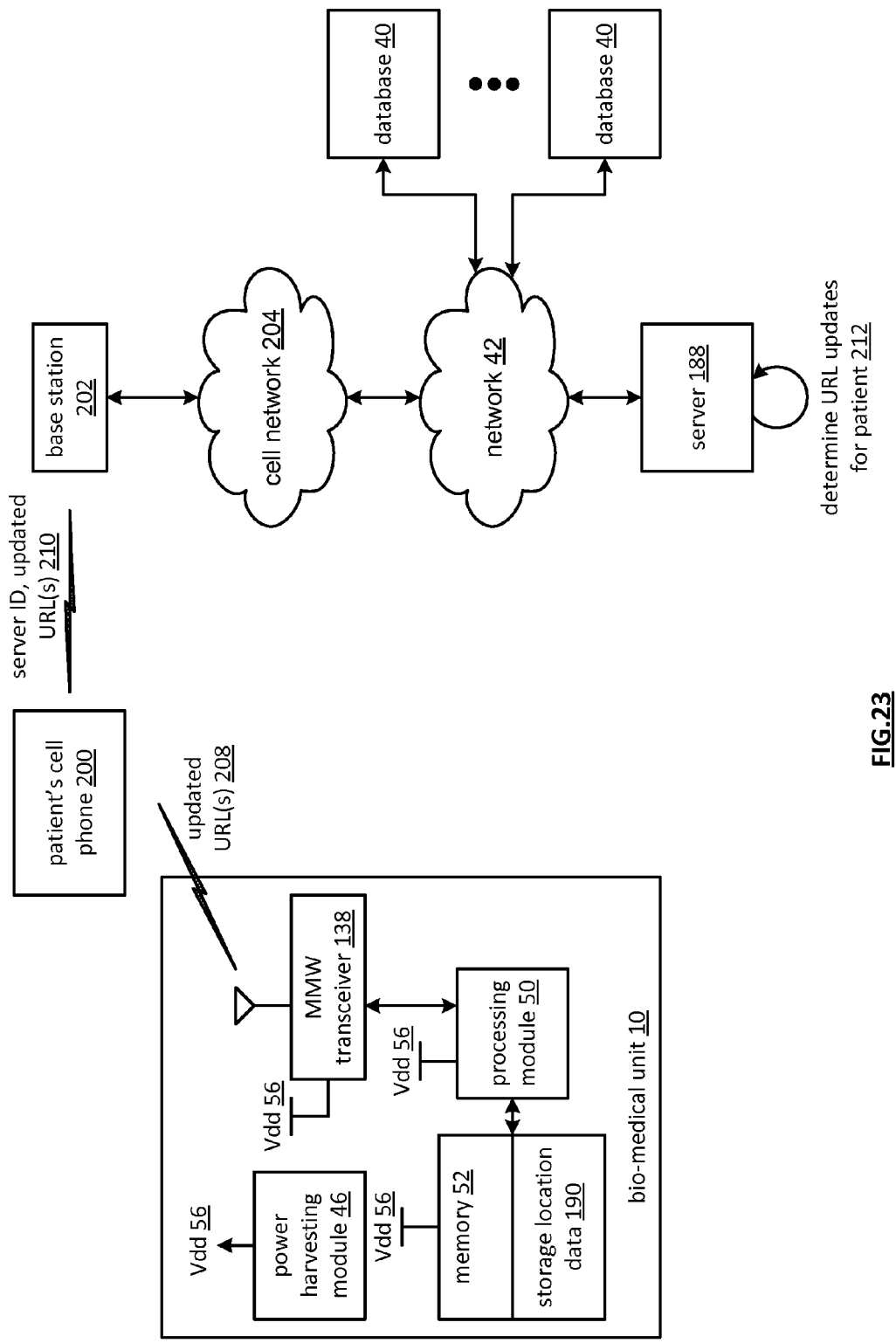
FIG. 23 is a diagram of an embodiment of a network of bio-medical units collecting ultrasound data in accordance with the present invention.

FIG. 23 is a diagram of another embodiment of a system that includes one or more bio-medical units 10, the patient's cell phone 200, a WAN communication device 34, a service provider's computer 186, a network 42, one or more databases 40, and a server 188. The bio-medical unit 10 includes a power harvesting module 46, a processing module 50, memory 52, and a MMW transceiver 138. The memory 52 is storing storage location data 190 for the patient. Note that the bio-medical unit 10 may be implanted in the patient, on the patient's body, or on the patient's person (e.g., in a medical tag, a key chain, etc.).

The data 190 may include one or more URLs that identify locations of the patient's medical records. For example, one URL may be for the patient's prescription records, another may be for hospitalizations, another for general office visits, etc. In this regard, the bio-medical unit is an index to easily access the patient's medical history.

To update the URL(s) in the bio-medical unit 10, the server 188 determines when an update is needed 212. When an update is needed, the server 188 generates an update message that includes the identity of the patient's cell phone 200, the updated URL data 208, and the identity of the bio-medical unit 10. The server 188 provides the update message to the patient's cell phone 200 via the network 42 and a base station 202. The patient's cell phone 200 processes the update message and, when validated, provides the updated URL data 208 to the bio-medical unit 10 for storage in memory 52 as stored updated patient URL(s) 206.

As may be used herein, the terms "substantially" and "approximately" provides an industry-accepted tolerance for its corresponding term and/or relativity between items. Such an industry-accepted tolerance ranges from less than one percent to fifty percent and corresponds to, but is not limited to, component values, integrated circuit process variations, temperature variations, rise and fall times, and/or thermal noise. Such relativity between items ranges from a difference of a few percent to magnitude differences. As may also be used herein, the term(s) "coupled to" and/or "coupling" and/or includes direct coupling between items and/or indirect coupling between items via an intervening item (e.g., an item includes, but is not limited to, a component, an element, a circuit, and/or a module) where, for indirect coupling, the intervening item does not modify the information of a signal but may adjust its current level, voltage level, and/or power level. As may further be used herein, inferred coupling (i.e., where one element is coupled to another element by inference) includes direct and indirect coupling between two items in the same manner as "coupled to". As may even further be used herein, the term "operable to" indicates that an item includes one or more of power connections, input(s), output(s), etc., to perform one or more its corresponding functions and may further include inferred coupling to one or more other items. As may still further be used herein, the term "associated with", includes direct and/or indirect coupling of separate items and/or one item being embedded within another item. As may be used herein, the term "compares favorably", indicates that a comparison between two or more items, signals, etc., provides a desired relationship. For example, when the desired relationship is that signal 1 has a greater magnitude than signal 2, a favorable comparison may be achieved when the magnitude of signal 1 is greater than that of signal 2 or when the magnitude of signal 2 is less than that of signal 1.

The present invention has also been described above with the aid of method steps illustrating the performance of specified functions and relationships thereof. The boundaries and sequence of these functional building blocks and method steps have been arbitrarily defined herein for convenience of description. Alternate boundaries and sequences can be defined so long as the specified functions and relationships are appropriately performed. Any such alternate boundaries or sequences are thus within the scope and spirit of the claimed invention.

The present invention has been described above with the aid of functional building blocks illustrating the performance of certain significant functions. The boundaries of these functional building blocks have been arbitrarily defined for convenience of description. Alternate boundaries could be defined as long as the certain significant functions are appropriately performed. Similarly, flow diagram blocks may also have been arbitrarily defined herein to illustrate certain significant functionality. To the extent used, the flow diagram block boundaries and sequence could have been defined otherwise and still perform the certain significant functionality. Such alternate definitions of both functional building blocks and flow diagram blocks and sequences are thus within the scope and spirit of the claimed invention. One of average skill in the art will also recognize that the functional building blocks, and other illustrative blocks, modules and components herein, can be implemented as illustrated or by discrete components, application specific integrated circuits, processors executing appropriate software and the like or any combination thereof.

What is claimed is:

1. An implantable bio-medical unit comprising:
a power harvesting module operable to convert an electromagnetic signal into a supply voltage;
memory powered by the supply voltage;
a transceiver powered by the supply voltage; and
a processing module powered by the supply voltage, wherein the memory, transceiver, and processing circuitry are operable to:
communicate with an external device regarding a medical matter;
retrieve data storage location information regarding the medical matter from the memory; and
communicate the data storage location information regarding the medical matter to the external device.

2. The implantable bio-medical unit of claim 1, wherein the memory, transceiver, and processing circuitry are further operable to:
receive additional data storage location information from the external device;
aggregate the additional data storage location information with the data storage location information to produce updated data storage location information; and
store the updated data storage location information in the memory.

3. The implantable bio-medical unit of claim 1, wherein the data storage location information addresses a plurality of differing storage locations.

4. The implantable bio-medical unit of claim 1, wherein the data storage location information addresses information regarding previous medical matters associated with a host body.

5. The implantable bio-medical unit of claim 1, wherein the memory, transceiver, and processing circuitry are further operable to:
generate a communication initiation message to initiate the communication with the external device, wherein the external device is a service provider communication device;
process a communication response message to verify authenticity of the service provider communication device; and
when the authenticity of the service provider is verified, transmit the data storage location information regarding the medical matter to the service provider communication device.

6. The implantable bio-medical unit of claim 1, wherein the memory, transceiver, and processing circuitry are further operable to convert an inbound signal into a data storage location information request regarding the medical matter received from a cellular telephone affiliated with the implantable bio-medical unit.

7. The implantable bio-medical unit of claim 1, wherein the data storage location information comprises at least one of:
a local area network address;
a wide area network address;
a web page address; and
a uniform resource locator (URL).

8. The implantable bio-medical unit of claim 1, wherein the memory, transceiver, and processing circuitry are further operable to:
convert an inbound wireless signal into an inbound signal;
convert the inbound signal into a request for the data storage location information regarding the medical matter;
convert the data storage location information regarding the medical matter into an outbound signal; and
convert the outbound signal into an outbound wireless signal.

9. The implantable bio-medical unit of claim 1, wherein the medical matter comprises one or more of:
image data of at least a portion of the host body;
information regarding identity of the host body;
medication prescriptions for the host body;
physical examination data of the host body;
operations performed on the host body; and
blood test results of the host body.

10. An implantable bio-medical unit comprising:
a power harvesting module operable to convert an electromagnetic signal into a supply voltage;
memory powered by the supply voltage and operable to store a plurality of medical matters regarding a host body including a medical matter;
a transceiver powered by the supply voltage; and
a processing module powered by the supply voltage, wherein the memory, transceiver, and processing circuitry are operable to:
convert an inbound signal into a request for data storage location information of the medical matter;
retrieve the data storage location information for the medical matter from the memory based on the request; and
convert the data storage location information for the medical matter into an outbound signal.

11. The implantable bio-medical unit of claim 10, wherein the memory, transceiver, and processing circuitry are further operable to:
convert an inbound wireless signal into the inbound signal; and
convert the outbound signal into an outbound wireless signal.

12. The implantable bio-medical unit of claim 10, wherein the memory, transceiver, and processing circuitry are further operable to:
determine an identity of a source of the request;
when the source of the request is an affiliated cellular telephone, retrieve the data storage location information for the medical matter from memory; and
when the source of the request is a service provider communication device, execute an authentication process to authenticate the service provider communication device and, upon authentication, retrieve the data storage location information for the medical matter from memory.

13. The implantable bio-medical unit of claim 10, wherein the data storage location information comprises at least one of:
a local area network address;
a wide area network address;
a web page address; and
a uniform resource locator (URL).

14. The implantable bio-medical unit of claim 10, wherein the medical matter comprises one or more of:
image data of at least a portion of the host body;
information regarding identity of the host body;
medication prescriptions for the host body;
physical examination data of the host body;
operations performed on the host body; and
blood test results of the host body.

15. A method for execution by a cellular telephone, the method comprising:
- establishing a wireless communication link with a bio-medical unit;
- via the wireless communication link, transmitting a retrieval command regarding a medical matter of a host body associated with the bio-medical unit that includes a request for data storage location information for the medical matter;
- receiving, via the wireless communication link, the data storage location information; and
- initiating a cellular telephone communication to retrieve data regarding the medical matter based on the storage location information.

16. The method of claim 15, wherein the data storage location information comprises at least one of:
- a local area network address;
- a wide area network address;
- a web page address; and
- a uniform resource locator (URL).

17. The method of claim 15, wherein the medical matter comprises one or more of:
- image data of at least a portion of the host body;
- information regarding identity of the host body;
- medication prescriptions for the host body;
- physical examination data of the host body;
- operations performed on the host body; and
- blood test results of the host body.

18. The method of claim 15, further comprising, when the command is a storage command, including in the command an instruction to store the data storage location information for the medical matter.

19. The method of claim 18, further comprising:
- receiving a download instruction from a remote medical device via a cellular telephone communication; and
- in response to the download instruction, generating the storage command.

20. The method of claim 15, further comprising:
- receiving additional data storage location information;
- transmitting the additional data storage location information to the implantable bio-medical device for storage.

* * * * *